(12) United States Patent
Petrich et al.

(10) Patent No.: US 9,329,128 B2
(45) Date of Patent: May 3, 2016

(54) TEST ELEMENT FOR DETECTING AN ANALYTE IN A SAMPLE

(71) Applicant: ROCHE DIABETES CARE, INC., Indianapolis, IN (US)

(72) Inventors: Wolfgang Petrich, Bad Schoenborn (DE); Luis David Bedon-Gomez, Bogotá (CO)

(73) Assignee: Roche Diabetes Care, Inc., Indianapolis, IN (US)

( * ) Notice: Subject to any disclaimer, the term of this patent is extended or adjusted under 35 U.S.C. 154(b) by 106 days.

(21) Appl. No.: 14/054,563

(22) Filed: Oct. 15, 2013

(65) Prior Publication Data

US 2014/0045203 A1  Feb. 13, 2014

Related U.S. Application Data

(60) Division of application No. 13/102,343, filed on May 6, 2011, now Pat. No. 8,574,514, which is a continuation of application No. PCT/EP2009/064758, filed on Nov. 6, 2009.

(30) Foreign Application Priority Data

Nov. 7, 2008  (EP) ..................................... 08168666

(51) Int. Cl.
*G01N 21/64*  (2006.01)
*B01L 3/00*  (2006.01)
*G01N 21/84*  (2006.01)
(Continued)

(52) U.S. Cl.
CPC .......... *G01N 21/6428* (2013.01); *B01L 3/5027* (2013.01); *G01N 21/8483* (2013.01); *G01N 33/526* (2013.01); *G01N 33/552* (2013.01); *B01L 3/502707* (2013.01); *B01L 3/502746* (2013.01); *B01L 2200/16* (2013.01);
(Continued)

(58) Field of Classification Search
CPC ............ G01N 21/8483; G01N 33/525; G01N 2021/0346; G01N 2021/177; G01N 2021/478; G01N 2021/5919; G01N 2021/5923; G01N 2021/593; G01N 2021/5934; G01N 2021/8488; G01N 2035/00039; G01N 2035/00108
See application file for complete search history.

(56) References Cited

U.S. PATENT DOCUMENTS 3,980,437 A * 9/1976 Kishimoto et al. ........... 422/404
4,057,394 A * 11/1977 Genshaw ........................ 435/66
(Continued)

FOREIGN PATENT DOCUMENTS

CN  1573331 A  2/2005
DE  19844500 A1  3/2000
(Continued)

*Primary Examiner* — Sally Merkling
(74) *Attorney, Agent, or Firm* — Harness, Dickey

(57) ABSTRACT

The invention relates to a test element for detecting at least one analyte in a sample, in particular for detecting at least one metabolite in a bodily fluid. The test element comprises at least one test field with a test field surface. The test field comprises at least one detection reagent that is adapted to undergo a detectable reaction in the presence of the analyte. The test element further comprises at least one distribution element that has at least one distribution surface facing the test field surface. Between the distribution surface and the test field surface is at least one capillary gap, wherein the capillary gap is adapted to allow a layer of the sample with a layer thickness of no more than 50 µm to form within the capillary gap.

4 Claims, 9 Drawing Sheets

(51) Int. Cl.
*G01N 33/52* (2006.01)
*G01N 33/552* (2006.01)

(52) U.S. Cl.
CPC . *B01L 2300/0825* (2013.01); *B01L 2400/0406* (2013.01); *B01L 2400/084* (2013.01)

(56) References Cited

U.S. PATENT DOCUMENTS

| | | | |
|---|---|---|---|
| 4,791,461 | A | 12/1988 | Kishimoto et al. |
| 5,051,237 | A | 9/1991 | Grenner et al. |
| 5,846,837 | A | 12/1998 | Thym et al. |
| 5,851,838 | A | 12/1998 | Vetter et al. |
| 6,707,554 | B1 * | 3/2004 | Miltner et al. ............... 356/433 |
| 7,008,799 | B1 | 3/2006 | Zimmer et al. |
| 2002/0119486 | A1 | 8/2002 | Oberhardt |
| 2003/0068666 | A1 | 4/2003 | Zweig |
| 2004/0071331 | A1 | 4/2004 | Lawless et al. |
| 2005/0147531 | A1 | 7/2005 | Buechler |

FOREIGN PATENT DOCUMENTS

| | | |
|---|---|---|
| EP | 0348006 A2 | 12/1989 |
| EP | 0821235 A2 | 1/1998 |
| EP | 1635170 A1 | 3/2006 |
| EP | 1733792 A1 | 12/2006 |
| WO | 9923475 A1 | 5/1999 |

* cited by examiner

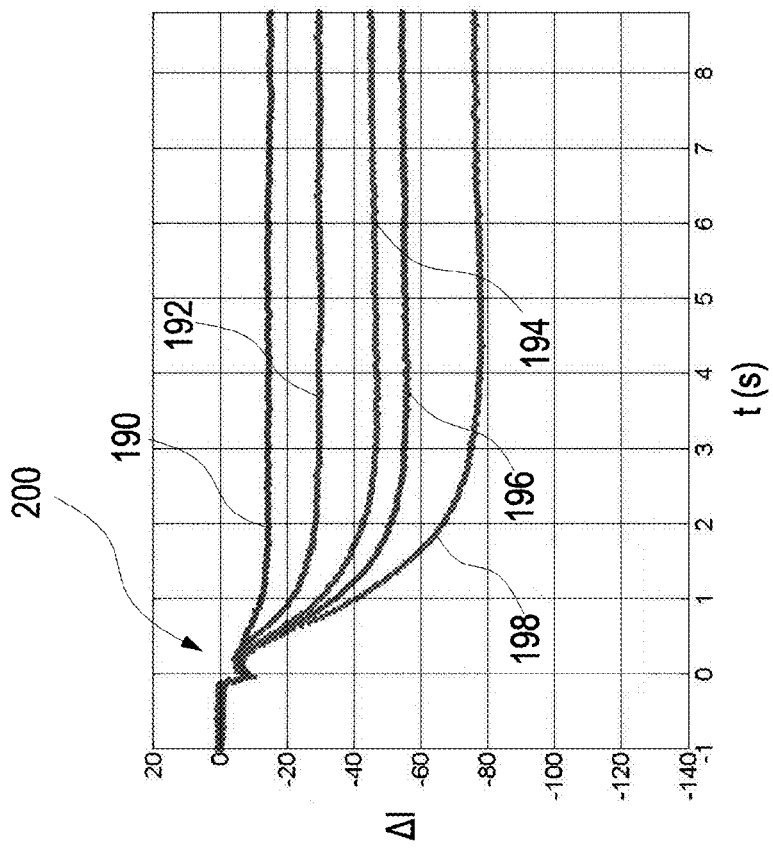
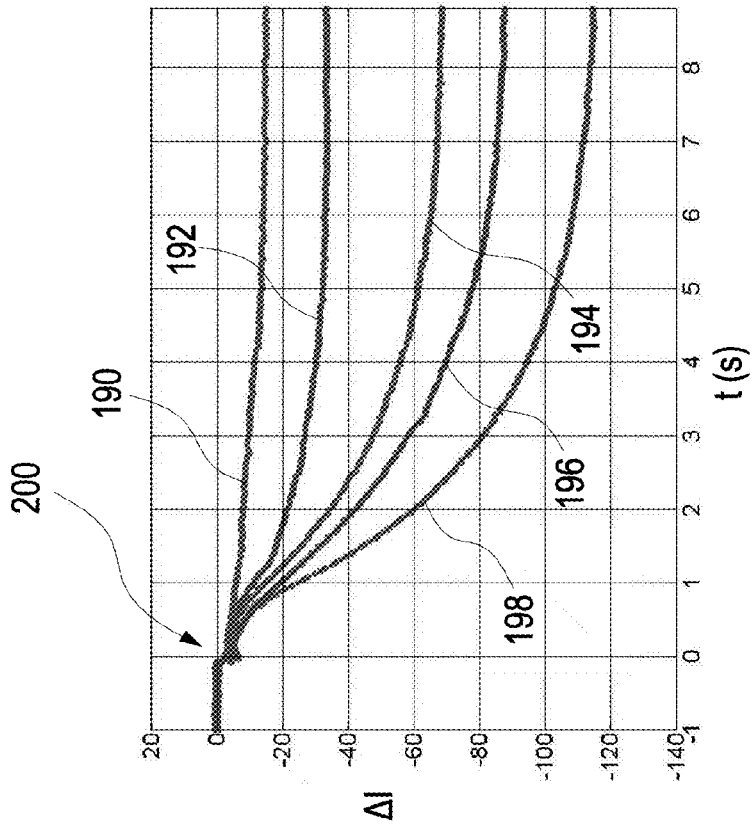
Fig. 6 A
Fig. 6 B

TEST ELEMENT FOR DETECTING AN ANALYTE IN A SAMPLE

CROSS-REFERENCE TO RELATED APPLICATIONS

This application is a divisional of U.S. patent application Ser. No. 13/102,343, filed May 6, 2011, which is a continuation of International Application No. PCT/EP2009/064758, filed Nov. 6, 2009, which claims the benefit and priority of European Patent Application No. 08168666.9, filed Nov. 7, 2008. The entire disclosures of the above applications are incorporated herein by reference.

BACKGROUND

The invention relates to a test element, a device, and a process for detecting at least one analyte in a sample. Test elements, devices, and processes of this kind are used in particular for detecting metabolites in body fluids. The following invention focuses on the detection of glucose in a body fluid, more particularly blood and/or interstitial fluid. However, in principle, other types of samples are also usable, for example other types of body fluids, such as urine or saliva for example, and also other types of analytes, such as cholesterol, lactate, coagulates or similar for example. In addition to being applied in medical diagnostics, the test elements, devices, and processes according to the invention may be used in other areas in principle, for example in other areas of science and technology, more particularly in chemical analysis for example.

SUMMARY

Many areas of science and technology require reliable and rapid qualitative and/or quantitative detection of one or more analytes in a sample, for example a fluid and/or gaseous sample. The present invention focuses on analyses in medical diagnostics, more particularly in diabetes prevention and diabetes treatment. In the context of diabetes prevention and/or diabetes treatment, it is normally necessary to determine rapidly and reliably the blood sugar level at least once a day, usually multiple times, in order to be able to take corresponding countermeasures in the event of deviations from the normal value. In order for these measures not to affect the daily routine of the patient more than necessary, devices and processes have been developed which enable blood sugar determination not only in a clinical environment but also, for example, at the workplace, at home, or during leisure activities. In addition, devices and processes are also known which are used in the clinical environment.

Devices and processes of this kind are normally based on the use of one or more test elements. These test elements are known and available in different forms, to which the present invention as a whole is applicable. For example, test elements in the form of test strips, test tapes, test disks, foldable test elements (for example, according to the Leporello principle) or in other forms are known. Hereinafter, the invention will be described substantially with reference to test strips, but other embodiments are also possible in principle.

Test elements normally comprise one or more test fields having at least one analyte-specific detection reagent. Said detection reagent is selected and designed to carry out a detectable reaction in the presence of the analyte to be detected. A detectable reaction is hereinafter understood to mean a reaction which is detectable by means of at least one physical and/or chemical detection process, preferably by means of a physical detection process. For example, reactions are known which can be detected optically and/or electrochemically. For example, reactions can be used here in which at least one detection substance is formed which can be detected optically and/or electrochemically.

For example, U.S. Pat. No. 5,846,837, Thym et al., issued Dec. 8, 1998, describes a diagnostic test support having a support layer. On the support layer, there is arranged a detection layer which contains the reagents required for determining the analyte in a fluid sample. Furthermore, the diagnostic test support comprises a meshwork (spreading mesh) which covers the detection layer and which is larger than the detection layer and is attached to the support layer. The meshwork is hydrophilic, but not capillary-active on its own, and comprises an inert cover made of sample-impermeable material on the areas extending beyond the detection layer.

However, production of the test support described in U.S. Pat. No. 5,846,837 having the spreading mesh requires an additional process step, such as application of the spreading mesh. In addition, the use of the spreading mesh can have an adverse effect on the space designed for the test support, since the spreading mesh provides a fluid reservoir for the sample, which must not go below a certain minimum thickness. Thus, as a rule, the thickness of the test support increases by, for example, 5 μm owing to the use of a spreading mesh, and this may already have a noticeable adverse effect on, for example, stored test elements. A further problem when using spreading meshes is that they may influence the homogeneity of detection in optical detection processes. For example, color changes may result in depiction of the spreading meshes, i.e., in irregular discoloration. The use of spreading meshes thus normally implies technical and commercial challenges which may be undesired.

Furthermore, for diagnostic systems, such as glucose measurement systems for example, the technical demands on certain constraints of the systems and of the measurement processes to be carried out therewith are constantly escalating. Thus, there is an increasing trend toward miniaturization of the measurement systems, especially with respect to an ever decreasing sample volume. Furthermore, there is a growing desire for speed in the measurement process and, at the same time, a demand for robustness. In addition, the processes and devices are under constantly growing cost pressure.

A more particular problem which is caused in particular by the described escalating requirements is a uniform, extensive, and rapid distribution (spreading) of small blood samples on the test fields having the reagent layer on the test elements, for example glucose test strips. Particularly in the case of the current photometric dry tests, a low blood amount manifests itself in only a partial wetting of the test fields, which is caused in particular by an often insufficient wettability of the test fields or of the reaction layers therein. Meshworks, also referred to as "spreading meshes," as described in U.S. Pat. No. 5,846,837, for example, and which serve to improve wettability, in this regard enable the problem to be alleviated, but themselves do not guarantee a uniform, extensive wetting of the test fields. In addition, the system, more particularly the test element with the sample, remains an open system which is dependent on, for example, fluctuations in the volume of the sample, for example the drop volume. More particularly, when these small volumes are applied over a large area, to spreading meshes for example, and thus provide a large surface for evaporation, this effect represents a challenge. In addition, there occurs in many cases buckling of the spreading meshes, which can result in inhomogeneities in the spreading behavior of the sample. Particularly in the case of small sample volumes, this inhomogeneity may manifest itself, as uncertainty in the determination of the glucose concentration. Detachment of the spreading mesh from the reagent layer can also lead to problems in this regard.

From the prior art, multiple test strip systems are additionally known which are designed as capillary test strips having a film structure. For example, U.S. Pat. No. 7,008,799, Zimmer et al., issued Mar. 7, 2006, describes an analytical test element having a capillary channel. The test element comprises an inert support, a detection element, and a channel capable of capillary fluid transport having a sample loading orifice and a ventilation orifice. The channel capable of capillary fluid transport is formed at least in part by the support and the detection element.

U.S. Patent Application Publication No. 2003/0068666 A1, Zweig, published Apr. 10, 2003, describes a diagnostic dry reagent test which is capable of reacting with a single blood drop and of detecting both glucose and beta-hydroxybutyrate. There is proposed, inter alia, a sandwich structure in which two PVC layers and a spacer are used to form an opening for receiving a blood sample, within which reagent fields are formed.

However, the test elements known from the prior art, such as the test elements in U.S. Pat. No. 7,008,799 or in U.S. Patent Application Publication No. 2003/0068666 A1, for example, still exhibit technical challenges. For example, U.S. Patent Application Publication No. 2003/0068666 A1 attempts to influence spreading behavior via optimization of the porosity of the reagent layer. However, the test element described therein still forms an open system having the above-presented problems, i.e., a system in which, firstly, sample fluid can evaporate and in which, secondly, the layer thickness, i.e., the volume for a given area, is not constant. Difficulties in uniformly wetting the test field can also be observed with the test element presented in U.S. Pat. No. 7,008,799. In addition, measurements have shown that the measured results may depend on the exact time difference between sample loading and attainment of the equilibrium state.

It is therefore an object of the present invention to provide a test element, a device, and a process for detecting at least one analyte in a sample, which at least largely avoid the disadvantages of known test elements, devices, and processes. More particularly, a very rapid and uniform change in the optical properties of the sample in a test field of the test element shall be ensured, and the reproducibility of the measured results and the independence of the measured results from the measurement times shall be increased.

This object is achieved by a test element, a device, and also a process having the features of the independent claims. Advantageous developments of the invention, which can be implemented individually or in combination, are presented in the dependent claims. The device can be set up to use a test element according to the invention as per one or more of the embodiments described hereinafter, and the process can be carried out using a device according to the invention and/or a test element according to the invention in one or more of the described embodiments. In this respect, for possible details of the device, reference can be made to the description of the possible details of the test element. More particularly, the device can comprise at least one test element according to the invention. Similarly, for the process and its optional embodiments, reference can be made to the description of the test element and/or the description of the device.

In a first aspect of the invention, there is proposed a test element for detecting at least one analyte in a sample. More particularly, the test element can be set up for detecting at least one metabolite in a body fluid. The subsequent description focuses in particular on the detection of glucose in a sample of a body fluid, more particularly in a blood sample. For generalizations of possible analytes and/or of possible samples, reference is made to the above description. The test element can be designed in a large variety of ways. Therefore, for the possible exterior manifestations of the test element, reference can likewise be made to the above description, so as to enable, for example, test strips, test tapes, test disks, or others of the above-described manifestations to be used. Without restricting further embodiments which are alternatively or additionally usable, there follows a description of, in particular, flat, strip-shaped test elements, i.e., test strips.

The test element comprises at least one test field having a test field surface. A test field is to be understood to mean a two- or three-dimensional region of the test element, which region is usable in principle for the detection of the analyte, which can be carried out qualitatively and/or quantitatively. More particularly, the test field can be designed as a dry test field. The test field comprises at least one detection reagent which is set up to carry out a detectable reaction in the presence of the analyte. In this regard, reference can, for example, be likewise made to the above description, for example the detection reagents mentioned in the prior art mentioned at the beginning. In addition to the at least one detection reagent which can carry out at least one analyte-specific reaction, the test field can comprise further substances, for example carrier substances, auxiliary substances, pigments, fillers, buffer substances, or similar. Hereinafter, no distinction is made between further substances which are likewise involved in the reaction for detecting the analyte, and the actual detection reagent. More particularly, the detection reagent can comprise an enzymatic detection reagent. Examples of such glucose-specific enzymatic detection reagents which may be mentioned are deoxy reductases (e.g., GlucDOR/PQQ), dehydrogenases, oxidases, or similar enzymes, for example glucose oxidase (GOD) or glucose dehydrogenase. The at least one detectable reaction is an optically detectable reaction. However, other types of reactions are also possible in principle. More particularly, it can be a reaction in which at least one detection substance is formed in the presence of the at least one analyte. Multiple detection substances can also be formed and/or used, which can be detected individually, in groups, or all together. Detection substances are thus substances which form owing to the at least one detection reaction and/or which are involved in the at least one detection reaction and which are detectable. By means of the at least one detection substance detected, it is possible, for example, to detect the at least one analyte quantitatively and/or qualitatively. However, detection processes and/or detection substances are also possible in which the detection of the at least one detection substance is not used or used not only for detecting the analyte, but alternatively for, for example, determining the volume layer of the sample thickness above the test field, as is yet to be described below.

The formation of said detection substance can then be detected directly or indirectly. For direct detection, a process is used which immediately detects the presence of the detection substance qualitatively and/or quantitatively. In contrast, for indirect detection, the presence of the at least one detection substance is deduced qualitatively and/or quantitatively via at least one notional, theoretical, or experimental intermediate step. For example, this can be effected via the presence and/or formation and/or reduction of further substances, where, for example, knowledge of at least one reaction mechanism makes it possible in turn to deduce the detection substance qualitatively and/or quantitatively, so as for said substance to be detected indirectly. A very well-known example of such a detection substance for the detection of blood glucose is NADH, i.e., the reduced form of nicotinamide adenine dinucleotide (NAD), which, for example, can be directly detected photometrically. Overall, however, reference can be largely made to the prior art for the embodiment of possible detection reagents and test fields.

In addition, the test element comprises at least one distributor element. Said distributor element comprises at least one distributor surface facing the test field surface, and so between the distributor surface and the test field surface there is formed at least one capillary gap which has a gap width, i.e., a thickness, perpendicular to the accessible test field surface. The capillary gap is set up such that a layer of the sample having a layer thickness of no more than 50 µm can form within said capillary gap. It is particularly preferred for the layer thickness to be no more than 20 µm. Layer thicknesses of 10 µm or less have been found to be particularly useful.

Said layer thickness can be formed in multiple ways. In the case of idealized and perfectly smooth surfaces, i.e., in the case of perfectly smooth test field and distributor surfaces, the maximum layer thickness which can form would exactly correspond to the distance between these surfaces, i.e., to the gap width of the capillary gap. Said gap width can be set by, for example, spacers. In the case of imperfect surfaces, these spacers would define, for example, the distance between the highest rises of the opposing surfaces. The gap width can be, for example, up to 50 µm, more particularly up to 30 µm, preferably up to 20 µm, and particularly preferably up to 10 µm. Normally, surface roughnesses are unavoidable or even desired. These surface roughnesses lead to the layer thickness of the sample, i.e., for example the fluid layer thickness of a fluid sample, being able to vary locally within the capillary gap between local maxima and local minima. The specified preferred layer thicknesses relate accordingly to the maximum layer thicknesses, which are preferably not exceeded. The surface roughnesses can even be used in a targeted manner. As is explained in more detail by way of example below, capillary gaps having a nominal gap width of "zero" shall also, according to the invention, be comprised by the invention, i.e., capillary gaps which are produced by the distributor surface lying immediately on top of the test field surface. In this case, the capillary gap is determined or produced only by the surface roughnesses of the test field surface and/or of the distributor surface. Owing to these unavoidable or deliberately generated irregularities, a capillary gap likewise forms which achieves the capillary effects described in more detail below. Such a system, in which the distributor surface lies directly on top of the test field surface, represents a "closed" system in which the sample volume directly above the test field surface, more particularly the sample volume per unit area, is greatly limited.

The test field can comprise in particular at least one test field material. Said test field material can preferably be formed such that it has an average grain size of less than 50 µm. Preferably, the average grain size can be less than 20 micrometers, more particularly less than 10 micrometers, and particularly preferably 5 micrometers or less. The term grain size will be generally explained in more detail below.

A distributor element is to be understood in principle to mean any formed element which provides the distributor surface facing the test field surface. Both the test field surface and the distributor surface are preferably substantially smooth and/or level so that preferably a level capillary gap forms. This at least one capillary gap can preferably extend across the entire test field surface. Alternatively, however, the test field surface can also be only partially covered. The formation of multiple individual capillary gaps is also possible in principle. The test field surface can, for example, comprise an analysis region, i.e., a region which is used for the analysis of the measurement, i.e., the detection of the at least one analyte. For example, this can, as will be explained in more detail below, be a region of the test field in which at least one detection region is formed on the support element. For example, for optical detection of the at least one analyte, the analysis region can be optically accessible straight through the detection region from the side of the test element facing away from the test field. The analysis region can accordingly be, for example, the projection of the detection region onto the test field surface. Preferably, the capillary gap essentially completely covers the analysis region of the test field surface. However, a merely incomplete covering is again also possible here in principle, for example by the distributor surface covering merely part of the analysis region and/or by multiple distributor surfaces being provided above the analysis region so that multiple capillary gaps form.

The test element is preferably designed as a flat, level test element, i.e., as a test strip. Preferably, the lateral extent of the test strip is considerably greater than the thickness of the test strip, for example by at least a factor of 10. The test field surface can have a lateral extent, wherein the capillary gap preferably extends substantially uniformly and/or parallel to said lateral extent. A lateral extent is to be understood to mean here the extent perpendicular to the thickness of the test field, wherein the lateral extent is preferably considerably greater than the thickness of the test field. The test field surface can preferably be level, so as for the capillary gap also to be preferably formed as a level capillary gap. However, curved test field surfaces are also possible in principle, for example test field surfaces which are round, arched, or formed in a similar manner. In this case as well, the capillary gap is preferably designed with a substantially constant gap width (i.e., averaged across surface roughnesses, for example), and so the distributor surface preferably follows the contour of the test field surface. The capillary gap can have a substantially constant gap width across the entire extent of the capillary gap, i.e., a constant gap width or a gap width which deviates from an average value by no more than 10%, preferably less.

Hereinafter, the layer thickness of the sample, which thickness can self-adjust in the capillary gap, and the gap width of the capillary gap, with reference to the above description, will no longer be conceptually distinguished from one another. Thus, when a gap width is discussed, this comprises in each case the possibility that this is the layer thickness of the sample within the capillary gap or the actual distance between the test field surface and the distributor surface.

The layer thickness or the capillary gap having the preferred thickness of 10 µm or less, for example a gap width h in the range of $0 \le h < 10$ µm, $0 \le h < 5$ µm, or $5$ µm$\le h < 10$ µm, has surprisingly been found to be, in practice, extremely advantageous in various aspects. Thus, this embodiment of the test element provides a way to accomplish the spreading of small sample volumes, more particularly fluid samples, of about 1 µl very rapidly in a cost-effective manner, for example by means of merely a slight modification of existing systems. For example, dispersal (spreading) can be accomplished within a period of less than 1 s. The sample fluid can be distributed over a space-saving area of, for example, up to 40 mm$^2$, preferably up to 20 mm$^2$. For example, use can be made of test field surfaces which have dimensions of 5 mm×4 mm or less. This rapid and homogeneous distribution of the sample on the test field surface is achieved in particular by capillary effects in the capillary gap. This is the capillary effect between the test field surface and the distributor surface, thus for example a capillary effect between two parallel plates. The test element can be set up to receive samples having a sample volume of less than 500 nl, preferably of less than 300 nl. This can, for example, be achieved by a corresponding dimensioning of the capillary gap. The sample volume in this preferred embodiment relates to the complete volume of sample received by the test element in a detection process. As an alternative or in addition, the sample volume in the capillary gap above the above-described analysis region, i.e., an analysis volume, can also be kept very small, for example at less than 500 nl, preferably less than 300 nl, and particularly preferably less than 100 nl. Analysis volumes of 50 nl and less, for example 10 nl or less, are also possible.

The test element according to the invention can, for example, be generated using known test elements which have to be modified only negligibly by additional application of the at least one distributor element. However, for the test element according to the invention, a spreading mesh on the test field surface may preferably be omitted. The test element can, for example, like conventional test strips, have at least one support element, more particularly a support strip. Said support element can, for example, comprise a plastics material, a ceramic material, a paper material, a composite material, or similar. The test field may in that case be applied to said support element. The support element can be used to assume a mechanically supportive function for the test element, for example to enable mounting of the test element during application of the sample and/or during a measurement. The capillary gap may in that case be arranged on the side of the test field opposing the support element. This can, for example, be achieved by the distributor element comprising at least one film element, more particularly at least one plastics film. The film element preferably has a closed surface which is preferably substantially impermeable to the sample. Preferably, the film element is nonporous, has a nonporous surface, or has pores having an average pore radius of no more than 5 μm, preferably of no more than one micrometer. Thus, the film element contrasts with, for example, conventional meshed materials, for example spreading meshes. In general, the distributor element and/or the distributor surface can comprise at least one material which is substantially impermeable to the sample.

For example, said film element can be applied to the test field surface. This application can, for example, be achieved such that the support element is covered by the film element only in a small section, preferably in a section which does not substantially protrude beyond the test field surface. In this way, the described capillary gap forms between the distributor element and the support element. Between the test field surface and the distributor surface, at least one distance element can be further arranged to ensure a constant thickness of the capillary gap, i.e., a constant and reproducible gap width. As described above, the capillary gap can, however, also be generated by placing the distributor surface directly on top of the test field surface.

The support element can be completely or partially produced from an optically nontransparent material. An optically nontransparent material is to be understood to mean a material which has a transmission of less than 5% in the visible and/or infrared and/or ultraviolet spectral range. Especially in this case, the detection of the reaction, for example by optical means, can be carried out in particular such that said detection is not carried out straight through the support element, but, for example, parallel and/or perpendicular to the lateral extent of the capillary gap, for example straight through the distributor element. For example, the distributor element can be at least partially optically transparent. For example, the distributor element can, as described above, comprise at least one film element, for example a film of a transparent plastic. Particular preference is given here to the use of polycarbonate films, for example POKALON® films. However, in principle, other plastics can also be used, preferably optically transparent plastics.

As an alternative or in addition, the detection of the at least one detectable reaction can, however, also be carried out completely or partially straight through the support element. Thus, the test element in, for example, the region of the test field on a side facing away from the capillary gap, more particularly a side of the support element facing away from the capillary gap, can have at least one detection region straight through which the detection of the at least one reaction can be carried out. Thus, the detectable reaction can comprise, for example, at least one optically detectable reaction which can be carried out from the side of the detection region. In this case, it is particularly preferred for the test field to comprise at least one optically nontransparent material, more particularly a reflector material, for example a pigment. For example, use can be made here of titanium dioxide particles. Said optically nontransparent material can be set up such that the capillary gap on the side of the detection region is not visible or only negligibly visible. In this way, it is possible, for example, to prevent optical detection from being influenced by the sample itself, for example hemoglobin in the sample. These interfering sample constituents can then be retained on, for example, the side of the test field facing away from the detection region, as is described in EP 0 821 233 A2 for example. In this way, it is possible to carry out, for example, photometric measurements which might be influenced by the sample itself.

Optical detection can, for example, be carried out by direct light illumination and/or direct light absorbance. As an alternative or in addition, optical detection can also be carried out by, for example, using one or more light guides. Thus, the at least one detectable reaction can in turn comprise at least one optically detectable reaction, wherein the test element further comprises at least one light guide which is set up to transport at least one detection light from the test field to an optical detector. A detection light is to be understood to mean a light in the infrared and/or visible and/or ultraviolet spectral range, which light is emitted and/or reflected and/or transmitted and/or absorbed and/or scattered by the test field and which light can contain information about the detectable reaction. For example, said detection light can be a luminescence, i.e., a fluorescence and/or a phosphorescence, and/or a reflected or remitted light. Optionally, the at least one light guide can further be set up to transport at least one interrogation light from a light source to the test field. Accordingly, the at least one light guide can, for example, comprise a separate light guide for the interrogation light and/or can use a dual-function light guide conductor for transporting the detection light and the interrogation light. The interrogation light can, for example, comprise a simple illuminating light which is reflected and/or transmitted by the test field, wherein, for example, at least one detectable reaction can be deduced from the spectral properties of the reflected and/or transmitted post-interrogation light, which is then used as the detection light. As an alternative or in addition, the interrogation light can, however, also comprise at least one excitation light in order, for example, to excite a luminescence in the test field and/or in the sample. Various embodiments are conceivable and are explained in more detail below by way of example.

The distributor element and/or the distributor surface are preferably designed such that they comprise at least one material which is substantially impermeable to the sample. For example, the distributor element itself can be produced from such an impermeable material. As an alternative or in addition, at least one coating can, however, also be provided which achieves this impermeability.

The distributor surface and preferably also the test field surface preferably have hydrophilic properties. In this way, the above-described capillary effect can be promoted further. These hydrophilic properties can, for example, be effected by a corresponding material selection and/or at least one coating and/or by surface treatments or similar. In this way, the distribution of the sample in the capillary gap and on the test field surface can be additionally sped up. Owing to these capillary properties, which provide for the distribution of the sample in the capillary gap and on the test field surface, a meshwork or spreading mesh, as is known from the above-described U.S. Pat. No. 5,846,837, for example, can preferably be completely omitted.

The sample can be introduced into the capillary gap in various ways, which can also be used in combination. Thus, the test element can comprise, for example, at least one application site for applying the sample, which site has a connection to the capillary gap, more particularly a fluid connection. Thus, said application site can be arranged, for example, directly at the capillary gap, for example by a region of the capillary gap having an application opening accessible from the outside. Said application opening can, for example, be arranged on a front side of the capillary gap. As an alternative or in addition, the application opening can, however, also be perpendicular to the capillary gap, for example by means of a corresponding recess in the distributor element itself and/or in the support element. For example, the distributor element can, as explained above, comprise a film element applied to the support element or to the test field, which film element can have, for example, at a front side of the test element a recess, for example a notch, into which the sample can be introduced. In this regard, reference can, for example, be made to the above-described U.S. Pat. No. 7,008,799.

As an alternative or in addition to this direct fluid connection between the application site and capillary gap, an indirect connection is also conceivable. For example, the test element can further comprise at least one transport device which is set up to transport the sample from the application site to the capillary gap. Said transport device can, for example, comprise a capillary. For example, said capillary can in turn be formed by a corresponding second capillary gap which, however, preferably does not adjoin the test field. Other embodiments are also possible in principle. As an alternative or in addition, the test element can also comprise at least one lancet element, more particularly a lancet element having a transport device, for example a closed capillary and/or a capillary gap, so that, for example, a sample can be collected as early as during the pricking procedure.

As described above, the test element according to the invention having the capillary gap has a multiplicity of advantages over known test elements. For example, a distributor element in the form of a film can be positioned according to the invention above the test field. A measurement can then, for example, be carried out straight through said film element. However, another type of measurement, i.e., of detecting the at least one detectable reaction, is also possible in principle, for example a measurement parallel to the capillary gap and/or a measurement straight through the support element.

The preferred gap widths of the capillary gap or the preferred layer thicknesses of about 10 µm or less have, as is explained in more detail below, been found in experiments to be optimal. Firstly, such capillary gaps and gap widths still induce, more particularly in the case of customary fluid samples, for example aqueous samples, for example blood samples, a good capillary effect which ensures a rapid distribution of the sample and thus a quick wetting of the test field surface, for example within less than 1 s. Secondly, it has, however, become apparent that an equilibrium state of customary detectable reactions can be reached more quickly with the mentioned gap widths, more particularly gap widths of 10 µm or less. This theory, of which the finding according to the invention of optimal gap widths is, however, independent in principle, is based on, for example, the above-described reactions, in which at least one detection substance is formed. Said detection substance, for example NADH, can, for example, be present in the test field itself in a bound form, for example in the form of a complex bond. For example, there can be present in the test field a complex in which NADH is bound to glucose dehydrogenase. In addition, the detection substance can, however, also diffuse into the sample itself, for example in the form of free NADH. The greater the sample volume available above the test field, in particular the greater the gap width, the longer lasting this diffusion is, since a certain concentration gradient range of the detection substance exists for a relatively long time. With increasing sample volume, more particularly with increasing gap width above the test field surface, two effects thus emerge: firstly, the time at which a diffusion equilibrium is reached and diffusion has become negligible is delayed, and so a measurement produces stable and reproducible results only after a considerably larger delay from introducing the sample into the test element. Secondly, in many cases, the detection substance diffused into the sample is no longer available for detection, since many of the conventional detection processes are based on the detection of the detection substance in the test field itself rather than in the sample. For example, customary, reflectometric optical detection processes, as described above, are based on back detection straight through a detection region of the support element. This is necessitated by sample constituents, such as hemoglobin for example, not being able to interfere with the optical detection in the case of such a back detection. However, if the detection substance diffuses into the sample, said substance may, owing for example to a limited penetration depth of the excitation light and/or of the illuminating beam, no longer be available for such a detection, and so overall the signal shift in the detection process for detecting the at least one reaction would decrease.

It has become apparent that the above-described preferred gap widths of 10 µm or less not only achieve a rapid distribution of small sample volumes on the test field surface, but also cause the diffusion equilibrium to be reached more rapidly, with, at the same time, a still acceptable signal shift. Thus, for a capillary gap having a gap width of 10 µm or less, an equilibrium of the reaction can be reached as early as within a few seconds and can be detected, and this can considerably speed up the measurement time. As explained above, this is caused in particular probably by the reaction kinetics and by the diffusion process of the detection substance, for example of NADH, which diffuses out of the test field into the sample, for example into the liquid layer present on the test field surface. Said diffusion process can be slowed down by the limited gap width and be reduced overall in its extent. As a result, a diffusion equilibrium between the sample and the test field is reached correspondingly quickly as a result.

However, the above-described effect of a rapid distribution of the sample on the test field surface and of an equilibrium being reached more quickly is influenceable by further factors. Thus, it has been found that particularly the grain size of the test field materials used in the test field can have a considerable influence on the described effects. The described effects were observed for the most part only for small grain sizes, more particularly for test field materials which had been subjected to a grinding process. Accordingly, it is proposed in a preferred embodiment of the invention that the test field comprises at least one test field material, and is preferably composed entirely of said test field material. A test field material can also be understood to mean a material mixture. Said test field material can, for example, comprise the above-described at least one detection reagent and also auxiliary substances, fillers, reflectors, or similar. In order to produce the test field material, it is possible, for example, to carry out initially a grinding process for the individual components, followed by a mixing process, or vice versa. More particularly, a previously prepared material mixture of the test field material can be subjected to a grinding process, for example in a bead grind and/or a jet grind.

It is particularly preferred for the test field material, which is normally in the form of particulate material, to have an average grain size which is in the range from 50 nm to 5 µm, more particularly between 25 nm and 5 µm. In contrast to conventional test field materials, which can have grain sizes in the range of several 10 µm, such test elements having finely grinded test chemistry or test materials exhibit particularly prominently the above-described positive effects. More particularly, in this way, the distribution of the sample on the test field surface can be greatly sped up, and speeding up the reaching of the equilibrium, more particularly for the described gap widths of 10 µm or less, is also distinctly promoted. By contrast, for grain sizes larger than 5 µm, a great irregularity is one observation which can be made, since the gap widths can also increase with the grain size. In addition, the reproducibility of the test elements decreases, and the wetting properties also worsen. The latter may be due in particular to an enlargement of the effective contact angle of the sample on the test field surface. By contrast, for grain sizes smaller than 50 nm, the wettability of the test field surface can likewise distinctly decrease. In addition, such finely grinded test field materials are technically feasible only with great difficulty.

The term "grain size", wherein in general the average grain size is meant here, shall be understood to mean, in the context of the present invention, the size of the individual particles of the test field material. In this regard, reference can, for example, be made to the corresponding standard EN ISO 14688. More particularly, the term "grain size" can be understood to mean the equivalent diameter which proceeds from the hypothetical assumption that the grains or particles of the test field material are present as beads. For example, said equivalent diameter can be specified by means of a screen diameter. For example, the average grain size can therefore be the grain size $d_{50}$, i.e., the median of the grain size distribution. The average grain size $d_{50}$ is therefore the equivalent diameter at which 50 percent by weight of the particles lie above or below. As an alternative or in addition, use can also be made of a hydrodynamic diameter as equivalent diameter and/or an aerodynamic diameter as equivalent diameter. In order to determine the grain size, a multiplicity of processes can be used, for example screening processes, sedimentation processes in water columns, light scattering processes (for example, scattering of laser light), or similar.

In conjunction with the grain size, there is also a preferred surface roughness of the test field surface. Thus, it is proposed that the test field comprises a test field material, wherein the test field material has, on the test field surface, a surface roughness of less than 50 µm, preferably of less than 25 µm, more particularly of up to 5 µm, and particularly preferably of up to 2 µm. Such surface roughnesses can, for example, be realized by using the above-described test field materials having the mentioned grain sizes. As an alternative or in addition, suitable application processes can, however, also be used in order to generate the test field material, for example to apply it to the support element. For this purpose, printing techniques, for example, can be used, more particularly screen printing, stencil printing, or pad printing. Doctor blade methods can also be used and also combinations of the mentioned techniques and/or other techniques.

The use of the grinded test field materials having the described grain sizes additionally results in an improved and more homogeneous wetting of the test field surface. In addition, boundary effects on the test field surface can be homogenized, for example by enabling a more homogeneous solubility of detection reagents used to be achieved. This higher homogeneity has in turn a positive impact particularly on the measurement of small sample volumes, since averaging via the inhomogeneities of the test field surface can result in distortion of the measured results.

The above-described finding that the appearance of a stationary state of the at least one detectable reaction, more particularly of the diffusion processes normally involved, is of considerable importance can also be used in a generalized manner. Thus, in a further aspect of the invention, a test element for detecting at least one analyte in a sample is proposed. More particularly, said test element can be designed according to one or more of the above-described embodiment variants. Accordingly, reference can be made to the above description for possible embodiments, which can be realized individually or in combination. However, other embodiments are also possible in principle. Again, the test element comprises at least one test field having a test field surface, wherein the test field comprises at least one detection reagent which is set up to carry out at least one detectable reaction in the presence of the analyte. The test element is set up according to the invention such that a stationary state of the detectable reaction is reached within a period of up to 4 seconds from an application of the sample, preferably within a period of up to 3 seconds.

A stationary state is to be understood to mean a state in which the detectable parameters of the detectable reaction change only insignificantly at least temporarily, for example for at least 1 second, more particularly 10 seconds, preferably 1 minute or more. For example, a plateau can appear in at least one detectable parameter. For remission measurements, for example, said plateau can be defined by a relative remission value changing by no more than around 1.5% relative remission within one second. For example, this can, as described above, imply a stationary state of diffusion reactions, for example a stationary state in which the concentration ratios of at least one detection substance within the test field and within the sample outside the test field no longer change or change only insignificantly. For example, in the stationary state, there can appear concentration ratios in which the concentrations of the at least one detection substance change by no more than 10%, more particularly by no more than 5%, and particularly preferably by no more than 3%.

As described above, this shortening of the mentioned period to up to 4 seconds can, for example, be effected by a constructive limiting of the layer thickness of the sample above the test field surface, for example to a layer thickness of no more than 50 µm, more particularly a layer thickness of no more than 20 µm, and particularly preferably to a layer thickness of 10 µm or less. In this regard, reference can again be made to, for example, the above description. For example, this can again be effected by using a corresponding capillary gap. However, in principle, other embodiments are also possible, i.e., embodiments without the mentioned limiting of the layer thickness and/or without the use of a capillary gap.

In a further aspect of the invention, the above-described finding that diffusion processes can considerably influence the measured result is used for improving the exactness of the measurements. Accordingly, there are proposed a device and a process for detecting at least one analyte in the sample, more particularly for detecting at least one metabolite in a body fluid. The device is set up to use at least one test element, more particularly a test element according to one or more of the above-described embodiments. Accordingly, reference can be made to the above description with regard to possible embodiments of the test element. The process is carried out accordingly using at least one test element, more particularly at least one test element according to the above description of one or more of the described embodiments, and so accordingly, reference can likewise be made to the above description. However, in principle, other types of test elements are also usable in the device and/or in the process, for example test elements without capillary gap. Furthermore, the process can be carried out using a device according to the invention.

The test element used has at least one test field having a test field surface for applying the sample. The test field in turn comprises at least one detection reagent which is set up to carry out a detectable reaction in the presence of the analyte. The detection reagent is set up such that at least one detection substance is formed in the detectable reaction, for example a detection substance according to the above description. More particularly, said detection substance can comprise NADH.

As explained above, particularly the diffusion of said detection substance into the sample is crucial in many detection reactions. Accordingly, it is proposed to determine directly and/or indirectly in the process the detection substance in the sample outside the test field. Said determination can be carried out qualitatively and/or quantitatively, and reference can be made to the above definition regarding the terms "direct" and "indirect". The determination can, for example, be carried out in the form of direct detection and/or in the form of indirect detection, more particularly quantitatively. Furthermore, it is proposed that the device is set up to then carry out the detection of the analyte taking account of said determination of the detection substance in the sample outside the test field. In other words, detection of the analyte can be carried out such that the parameter of diffusion into the sample outside the test field, unknown in previous detection processes, is now also considered. This can, for example, be done by correction factors being determined which consider said diffusion. As an alternative or in addition, other types of correction algorithms can also be applied in order to consider the extent of the diffusion of the detection substance into the sample outside the test field. For example, provided correction algorithms can be used, for example correction factors in electronic tables, corresponding to the detection of the detection substance in the sample outside the test field or similar. Considering the detection substance in the sample outside the test field makes it possible to consider, for example, variations in the fluid layer thickness, more particularly in the gap width, for example owing to manufacturing-associated tolerances in test element production.

To carry out said process, the device can, for example, comprise a calibration device which is set up to determine the detection substance in the sample outside the test field; for example, to detect it directly or indirectly. The device can in that case be correspondingly set up to carry out the detection of the analyte taking account of said determination of the detection substance in the sample outside the test field. For example, the device, more particularly the calibration device, can comprise for this purpose corresponding data processing equipment, for example a microcomputer, and also, if necessary, optionally one or more volatile and/or nonvolatile data memories, for example for storing a list of correction factors.

To determine, more particularly to detect, the detection substance in the sample outside the test field, use can be made of various processes and/or devices. As described above, the detection substance can, for example, be detected directly and/or also indirectly, for example by the (normally diffusion-associated) decrease in the detection substance and/or in a compound of the detection substance or a substance containing the detection substance within the test field being qualitatively and/or quantitatively detected.

A detection process can, for example, be based on the detection substance in the sample and in the test field having different properties with regard to an interaction with an interrogation light and/or with regard to the emission of the detection light. For example, spectral properties of the detection substance in the test field and in the sample may be distinguished from one another owing to environmental effects. As an alternative or in addition to such time-independent spectral effects, temporal spectral effects may also occur which can, for example, be detected by means of time-resolved measurements. Said temporal effects, which distinguish the detection substance in the sample outside the test field from the detection substance within the test field, can, for example, have an effect in different luminescence lifetimes, for example in different fluorescence lifetimes. For example, it has been observed that NADH, which normally exists in the form of a glucose dehydrogenase-NADH complex (GlucDH-NADH) within the test field, has a higher fluorescence lifetime than in a free form, for example within an aqueous fluid sample. There is, for example, a difference in the fluorescence lifetimes of almost an order of magnitude, and so detection substances within the sample outside the test field and within the test field can be distinguished from one another quantitatively by corresponding time-resolved measurements. The device can correspondingly be set up to detect the detection substance in the sample outside the test field by means of at least one time-resolved measurement, more particularly by means of at least one time-resolved optical measurement, more particularly a fluorescence measurement.

As described above, said determination of the detection substance in the sample outside the test field can also be used to carry out a calibration. For example, a calibration to tolerances in the gap width of the capillary gap can be performed. Accordingly, the device and, correspondingly, also the proposed process can be designed in particular such that the test element comprises at least one capillary gap connected to the test field for receiving and distributing the sample on the test field. For example, the capillary gap can be designed according to one or more of the above-described embodiments.

The calibration device can then be set up such that determining the detection substance in the sample outside the test field makes it possible to perform a calibration of the gap width of the capillary gap. This can, for example, also be achieved again by means of corresponding correction factors. This embodiment of the proposed process and of the proposed device can considerably improve overall accuracy of the detection of the at least one analyte, since the detection can therefore be at least largely independent of the sample volumes. Particularly an online calibration can be achieved which is carried out at the same time as the actual measurement or with just a slight time delay (for example of less than 1 s), and so, for example, the input of lot-specific information about the at least one test element into the device can be omitted. The device can, accordingly, be set up to carry out a calibration measurement immediately during, immediately before, or immediately after the actual measurement, by means of which the required calibration information can be obtained. As a result, it is, for example, possible to greatly simplify the production processes for the test elements, since lower requirements for the tolerances of the test elements can be set.

DRAWINGS

Further details and features of the invention can be found in the following description of preferred exemplary embodiments, more particularly in connection with the subclaims. Here, the respective features can be achieved on their own or in combination with one another. The invention is not restricted to the exemplary embodiments. The exemplary embodiments are depicted diagrammatically in the figures. The same reference numbers in the individual figures indicate the same elements or elements which are functionally similar or correspond to one another with regard to their functions. Details of the figures are as follows:

FIGS. 6A and 6B show examples of a time course of a photometric measurement on test elements having grinded and ungrinded test field materials;

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
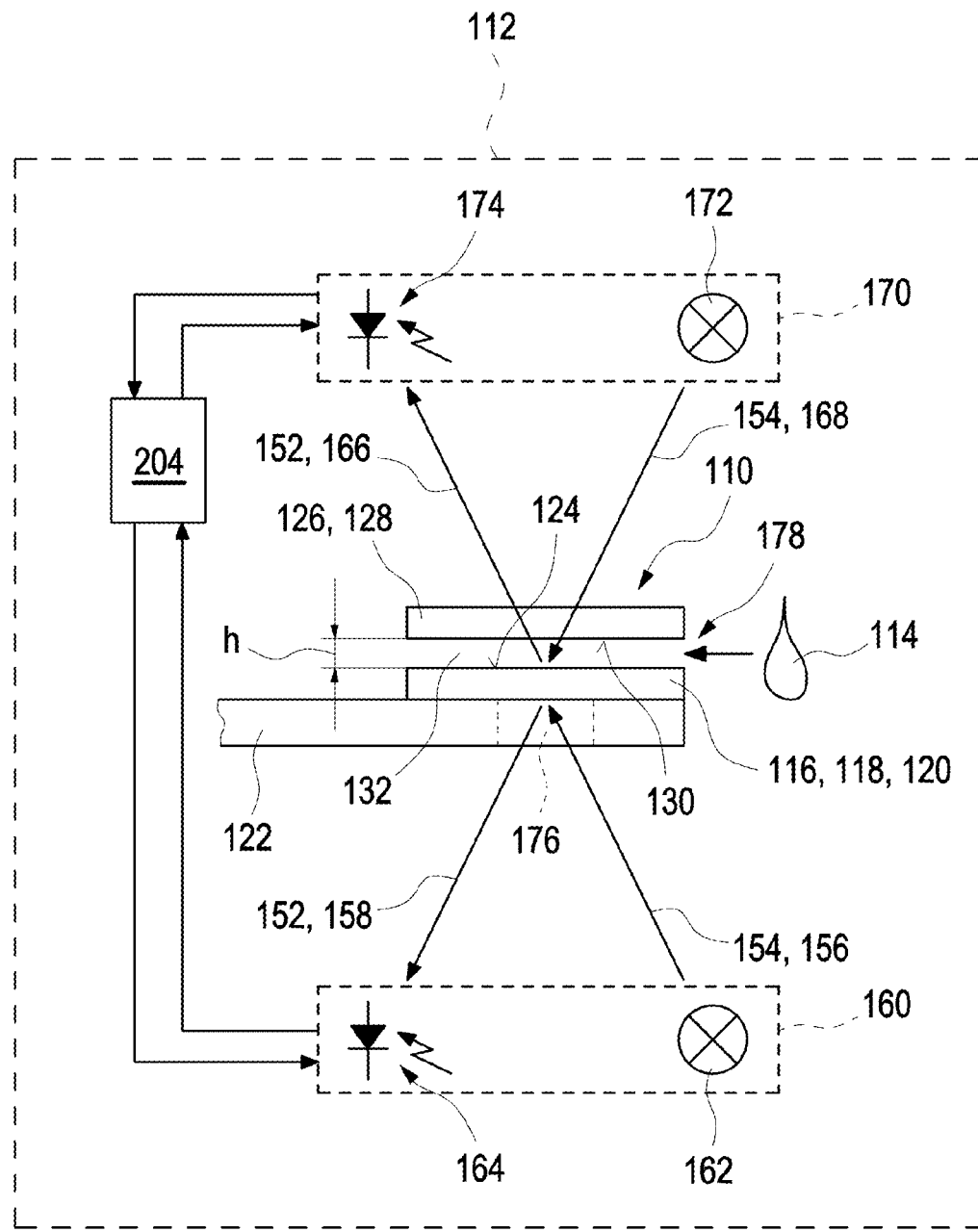
FIG. 1 shows an exemplary embodiment of a device according to the invention for detecting an analyte in a body fluid with a first exemplary embodiment of a test element.

FIGS. 1, 2A and 2B and FIG. 3 depict three different exemplary embodiments of test elements 110 according to the invention for detecting an analyte in a sample. Furthermore, FIG. 1 shows symbolically a device 112 for detecting the analyte in a body fluid, which device uses the test element 110. Using the example of said device 112, a process according to the invention for detecting the analyte in the sample shall also be presented.

Furthermore, it shall be assumed that the sample is a sample of a body fluid, more particularly a blood sample. Said blood sample is depicted symbolically by means of a blood drop in FIG. 1 and FIG. 2B and indicated by the reference number 114, and it is assumed that the analyte to be detected in said blood drop 114 is, for example, blood glucose. However, as explained above, it should be pointed out that other types of samples can also be tested and that detection of other types of analytes can also be carried out.

The test elements 110 each have a test field 116. Said test field 116 comprises a test field material 118 having at least one detection reagent 120. Said detection reagent 120 is set up to carry out an analyte-specific, detectable reaction when said reagent comes into contact with the analyte to be detected. For example, said detection reagent 120 can, as explained above and as described in the prior art for example, comprise one or more enzymes, auxiliary substances, fluorophores, or similar. For the detection of blood glucose, the detection reagent 120 can, for example, comprise glucose dehydrogenase as enzyme and NAD+ as coenzyme. In the presence of glucose, NADH forms, which can act as a detection substance and which can be detected in a free or bound form by, for example, photometric measurements and/or luminescence measurements, as is explained in more detail below.

The test field 116 has been applied to a support element 122 in the exemplary embodiment according to FIG. 1. Said support element 122 can, for example, be designed as a strip-shaped test support element 122, with, as explained above, other embodiments also being possible. The test field 116 has a test field surface 124 facing away from the support element 122. Hereinafter, it shall be assumed that said test field surface 124 is designed as a level surface, for example as a level test field surface having dimensions of 5×4 mm$^2$.

Above the test field surface 124, there is arranged in the exemplary embodiment according to FIG. 1 a distributor element 126 which is formed as a film element 128 in said exemplary embodiment and which is preferably transparent. Said distributor element 126 has a distributor surface 130 facing the test field surface 124. This distributor surface 130 is also preferably level and is preferably arranged parallel to the test field surface 124. Between the distributor surface 130 and the test field surface 124, there therefore forms a capillary gap 132, preferably a level capillary gap 132, which extends perpendicularly to the drawing plane in FIG. 1 and thus parallel to the test field surface 124 and its lateral extent. Said capillary gap 132 has a gap width which is indicated by h in FIG. 1. Said gap width can, for example, when surface roughnesses of the test field surface 124 and/or of the distributor surface 130 are disregarded and/or are negligible, correspond essentially to a layer thickness of a sample, more particularly a fluid sample, which is introduced into this capillary gap 132. Therefore, no conceptual distinction will be made hereinafter between the gap width of the capillary gap 132 and the layer thickness of the sample within the capillary gap 132, unless expressly pointed out.

Figure 2:
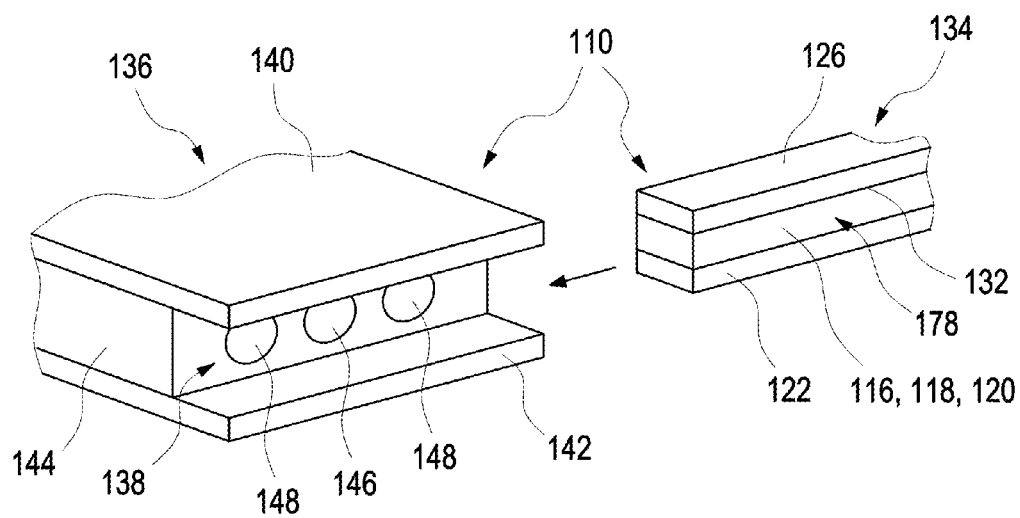
FIGS. 2A and 2B show various views of a second exemplary embodiment of a test element according to the invention.
Figure 2:
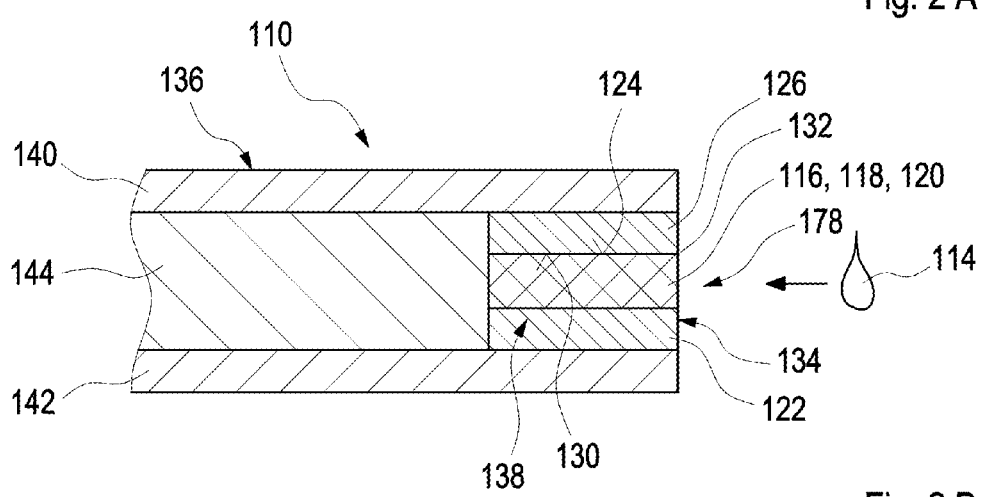

FIGS. 2A and 2B depict a second exemplary embodiment of a test element 110. FIG. 2A shows a perspective view, whereas FIG. 2B shows a sectional view from the side. Again, the test element 110 has, according to said exemplary embodiment, a test field 116 which has been applied to a support element 122. For possible details, reference can be made to the description of FIG. 1. Said test field 116 again has a test field surface 124, which faces away from the support element 122. Correspondingly, a distributor element 126 having a distributor surface 130 is again formed on the side opposite the support element 122. Between the distributor surface 130 and the test field surface 124, there forms again a capillary gap 132 of very small dimensions in FIG. 2B compared to the layer thickness of the test field 116. As described above, the distributor surface 130 can also lie directly on top of the test field surface 124, so as to form a closed system having the gap width of "zero", as described above.

In contrast to the exemplary embodiment according to FIG. 1, in which the support element 122 is considerably larger than the distributor element 126, the support element 122 and the distributor element 126 have approximately the same dimensions in the exemplary embodiment according to FIGS. 2A and 2B. For the support element 122 and for the distributor element 126, use can be made of similar or different materials, for example, in each case, optically transparent or else optically nontransparent materials. Particular preference is given to the use of plastics film materials, such as polycarbonates for example, more particularly POKALON®. The support element 122, the distributor element 126 and the test field 116 lying inbetween and also the capillary gap 132 form together in the exemplary embodiment according to FIGS. 2A and 2B a detection part 134 which can, for example, be designed with very small dimensions, for example of 300 μm×300 μm×4 mm. Furthermore, the test element 110 can comprise a coupling part 136 which can be used for mechanical mounting of the detection part 134. Said coupling part 136 can, for example at its front end, comprise a slot 138 into which the detection part 134 can be slid in. Said slot 138 can, for example, be formed by the coupling part 136 comprising a sandwich structure having an upper retaining piece 140, a lower retaining piece 142, and a coupling body 144 lying inbetween. As can be seen in particular from FIG. 2B, the retaining pieces 140, 142 in the region of the slot 138 protrude beyond the coupling body 144, thus forming in this region the slot 138 into which the detection part 134 can be slid in.

The retaining pieces 140, 142 can, for example, again be strip-shaped, for example made of a plastics, paper, ceramic, or composite material. A more complex layer structure is also possible. In the coupling body 144, which can, for example, comprise a plastics material, there are preferably embedded, as can be seen in FIG. 2A, light guides 146, 148, which end in the region of the slot 138 and which enable optical coupling to the detection part 134. In the depicted exemplary embodiment, there is provided a central light guide 146 which can guide interrogation light from a light source not depicted in FIGS. 2A and 2B, for example from a light source of the device 112, to the detection part 134 and there in particular to the test field 116. Said central light guide 146 is, in the depicted exemplary embodiment, surrounded symmetrically by two further light guides 148 which are set up to guide detection light from the detection part 134 to a detector which is likewise not depicted in FIGS. 2A and 2B, for example to a detector of the device 112. Various measurement principles are explained in more detail below. In the depicted exemplary embodiment, the coupling body 144 therefore acts not only as a distance piece between the retaining pieces 140, 142 and to form a mechanical slot 138, but also, at the same time, to provide optical coupling by means of the light guides 146, 148.

The fixing of the detection part 134 in the slot 138 can, for example, be achieved by means of a form fit, a force fit or a cohesive fit and also by means of combinations of the processes mentioned. For example, an adhesive can be used for fixing the detection part 134 in the slot 138. However, for many applications, the use of an adhesive is not desirable, since it, for example, can itself have fluorescence properties.

The depicted optical coupling, which can be made substantially parallel to the lateral extent of the test field 116 in the exemplary embodiment according to FIGS. 2A and 2B, can be facilitated by enabling the thickness of the test field 116 to be adapted in order to correspondingly position the ends of the light guides 146, 148, for example the fiber ends. Accordingly, a vertical orientation of the ends of the light guides 146, 148 can, for example, be set solely by the film thickness of the layer structure of the detection part 134.

Furthermore, in the layer structure, in which coupling is made substantially parallel to the lateral extent of the test field 116, for the support element 122 and/or the distributor element 126, use can also be made of optically nontransparent materials, for example black materials, for example black films. In this way, coupling of interfering ambient light into the light guides 146, 148 can be avoided for example. As an alternative or in addition, the upper retaining piece 140 and/or the lower retaining piece 142 can also be optically nontransparent, for example again comprise black films, in order to avoid and/or to reduce here as well coupling of interfering ambient light into the light guides 146, 148.

The light guides 146, 148 can, for example, comprise glass fibers and/or plastics fibers. However, other types of light guides are also usable in principle, for example light guides having another geometry. For example, light guides 146, 148 of this kind can be easily realized by means of microinjection molding. However, other techniques are also usable, for example insert molding of light guides 146, 148 with a matrix material of the coupling body 144.

Figure 3:
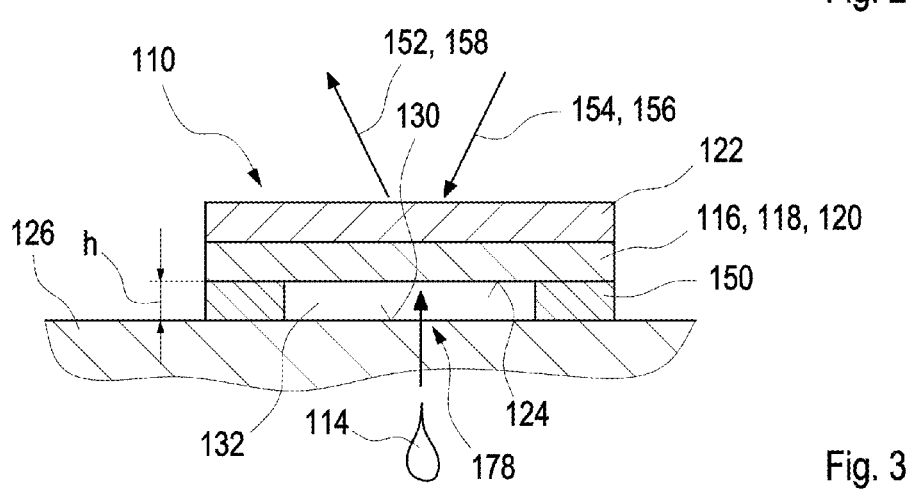
FIG. 3 shows a third exemplary embodiment of a test element according to the invention.

FIG. 3 depicts a third exemplary embodiment of a test element 110 according to the invention. Again, said test element 110 comprises a test field 116 having a test field surface 124, which field has been applied to a support element 122. For the embodiment of said test field 116, reference can, for example, again be made to the description of FIG. 1. Furthermore, the test element 110 again comprises a distributor element 126 opposite the test field surface 124, with a distributor surface 130 opposite the test field surface 124. Between the test field 116 and/or the support element 122 outside the test field 116 and the distributor element 126, it is possible for one or more distance elements 150 to be provided, as depicted in FIG. 3 and as can also be optionally realized in the exemplary embodiments according to FIGS. 1 and 2A and 2B. Said distance elements 150, which for example can again be made of a film material and for example can be cut out or punched out, can be used for generating a constant capillary gap 132 having an exactly defined gap width h. Preferably, this at least one distance element 150 is designed such that the capillary gap 132 is opened on at least two sides to enable pressure equalization and to promote a capillary effect.

The exemplary embodiment of the test element 110 according to FIG. 3 represents to a certain extent an inverse structure of the exemplary embodiment according to FIG. 1, since the support element 122 is considerably smaller than the distributor element 126 in the depicted exemplary embodiment. A mechanically supportive function can therefore be assigned to the distributor element 126 in the exemplary embodiment depicted in FIG. 3.

Furthermore, the exemplary embodiments in FIGS. 1, 2A and 2B and in FIG. 3 also show various forms of the detection of the analyte-specific reaction. In all cases, there is depicted an optical detection, which is particularly preferred in the context of the present invention. As an alternative or in addition, it would, however, be possible in principle to use other detection processes as well, for example electrochemical detection processes. In the depicted optical detection processes, at least one detection light originating from the test field 116 is received by a detector. Various types of detection light have been explained above. Thus, said detection light can, for example, comprise a light reflected, transmitted, or emitted from the test field 116 and/or combinations of the types of light mentioned. The above terminology relating to said detection light originating from the test field 116 comprises not only an output immediately from the test field surface 124 and/or from inside the test field 116 but also the possibility that said detection light originates from the sample 114 inside the capillary gap 132. This possibility is explained in more detail below.

The detection light is indicated symbolically by the reference number 152 in FIGS. 1 and 3. Depending on how said detection light 152 is generated, which is intended to demonstrate the analyte-specific reaction, it may be necessary to illuminate the test field 116 with an interrogation light 154. Said interrogation light 154 can interact with the test field 116 in different ways, and this, as described above, shall also comprise an interaction with the sample 114 in the capillary gap 132 above the test field surface 124. For example, said interrogation light 154 can be reflected and/or remitted and/or absorbed and/or scattered by the test field material 118 of the test field 116, and this for example is made use of for photometric measurements in customary test strips. For example, said remission can demonstrate a color change of the test field material 118, which change is caused by the analyte-specific reaction, for example by the formation of free or bound NADH as detection substance. Accordingly, the interrogation light 154 can, for example, comprise an illuminating beam 156, and the detection light 152 can comprise a remitted beam 158. Accordingly, the device 112 can, as depicted in FIG. 1, comprise a photometric measurement device 160 having a light source 162 for generating the illuminating beam 156 and having a detector 164 for detecting the remitted beam 158. The light source 162 and the detector 164 can be designed in different ways, for example by using lamps, light-emitting diodes, lasers, or combinations of the light sources mentioned and/or of other types of light sources and by using photodiodes, photocells, photonic amplifiers, or other types of detectors.

Furthermore, it is possible, as an alternative or in addition, for the detection light 152 to comprise, for example, a luminescence light 166. This option, which can also be realized in the other exemplary embodiments, is shown by way of example in FIG. 1. For example, said luminescence light 166 can be a fluorescence which is emitted by a detection substance formed in the analyte-specific reaction. For example, this can again be NADH in a free or bound form, as is explained in more detail below. To stimulate the luminescence, the optional interrogation light 154 can comprise an excitation beam 168, as is likewise indicated symbolically in FIG. 1. Said excitation beam 168 can, for example, like the interrogation light 154 as well in general, be adapted to the spectral properties of the detection substance to be detected. For example, as indicated in FIG. 1, the device 112 can comprise a luminescence measurement device 170 having a light source 172 and a detector 174, which are again indicated symbolically in FIG. 1. For the possible embodiments of the light source 172 and of the detector 174, reference can, for example, be made to the photometric measurement device 160. Thus, the photometric measurement device 160 with its light source 162 and its detector 164 can be adapted specifically to remission measurement, and in the same way, the luminescence measurement device 170 with its light source 172 and its detector 174 can be adapted specifically to luminescence detection. In general, it is also possible to receive detection light 152 having multiple wavelengths. Depending on the type of detection light 152, it is also possible in principle to omit an interrogation light 154.

The exemplary embodiments in the individual figures show that the detection light 152 can be detected in different ways, which can also be combined. As can be seen in FIGS. 1 and 3, the detection light 152 can, for example, be detected straight through the support element 122, and the device 112 can, for example, be arranged correspondingly on the side of the support element 122 opposite the test field 116. Accordingly, the support element 122 can, for example, as preferred in FIG. 3, be transparent at least in part for the detection light 152, for example by a transparent film being used for said support element 122, for example POKALON®. As an alternative or in addition, the support element 122 can, as shown in FIG. 1, also comprise in the region of the test field 116 a detection region 176 which can be transparent at least in part for the detection light 152. Said detection region 176 can, for example, comprise an opening in the support element 122 and/or an optically transparent material.

As depicted in FIGS. 1 and 3, the back measurement method, in which the detection light 152 is received straight through the support element 122 and, optionally, the interrogation light 154 also penetrates the support element 122, is particularly preferred for photometric measurements, more particularly remission measurements. However, it has become apparent, in blood samples in particular, that such photometric measurements may be influenced by the sample 114 itself, since hemoglobin, for example, can considerably influence such photometric measurements. Accordingly, it has been found, and is also known from the prior art, to be advantageous for the test field material 118 to comprise at least one pigment which acts as a reflector material and which is arranged at least in upper layers of the test field 116 facing the capillary gap 132. For example, titanium dioxide pigments can be used for this purpose. For example, the test field 116 can have a layer structure, as is known for example from the above-described prior art. Said pigments make it possible to retain red blood cells in the upper region of the test field 116 facing away from the support element 122 in order not to influence or to influence only minimally the photometric measurements on the side facing the support element 122. At the same time, the pigments act as reflector material to reflect the illuminating beam 156 illuminating the back side. The red blood cells on sides of the capillary gap 132 are then preferably not visible from the back side, i.e., from the support element 122.

As an alternative or in addition, use can be made of a measurement method shown in FIG. 1, which can also be realized in the other exemplary embodiments. In this measurement method, which, as described above, involves the detection of luminescence light 166 as detection light 152, a measurement can also be carried out straight through the distributor element 126, i.e., from the "front side", with regard to the test field surface 124. For this purpose, the distributor element 126 can be completely or partially optically transparent for the interrogation light 154 and/or parts of the interrogation light 154, for example by again using a film element 128, for example a POKALON® film. As is yet to be explained in more detail below, this type of detection is particularly favorable for luminescence light measurements.

Again, as an alternative or in addition, use can be made of the measurement method indicated in FIGS. 2A and 2B, in which the detection part 134 is inserted into the slot 138 such that the optical coupling in and out can be made parallel to the lateral extent of the test field 116. This type of coupling can also involve photometric measurements and/or luminescence measurements, for example analogously to the above-described measurement methods. It should be pointed out that, however, the embodiment depicted in FIGS. 2A and 2B can also be modified such that an optical coupling from other directions can be made, for example again perpendicular to the lateral extent of the test field 116. For this purpose, the detection part 134 in FIG. 2B, for example, can be rotated by 90° or by another angle on an axis perpendicular to the drawing plane.

The test elements 110 preferably have an application site 178 which is designed as a simple opening of the capillary gap 132 to the environment in the depicted exemplary embodiments. However, the application site 178 can also be designed in more complex ways, for example by using corresponding notches, openings, or similar, for example in the support element 122 and/or in the distributor element 126. Various embodiments are possible.

According to the invention, the capillary gap 132 is used to provide a cost-effective and efficient way of distributing (spreading) homogeneously even small sample volumes of, for example, 1 µl within a short time (for example in less than 1 s) across the test field surface 124. For this purpose, the capillary effect between the distributor surface 130 and the test field surface 124 is made use of by, for example, applying the distributor element 126 over the test field 116 (reaction layer) of a conventional glucose test strip. The test field surface 124 and/or the distributor surface 130 can, in order to increase the capillary effect, be additionally provided with hydrophilic properties. Thus, the distributor element 126 can, for example, be a hydrophilic film and/or comprise such a film, for example the transparent POKALON® already mentioned above. In this way, there can form a sandwich system which, for example, is wetted from an application site 178, for example at the edge of the test field 116. Thus, it is possible, via the capillary effect of the two surfaces 124, 130, to move and distribute the sample 114, for example blood, over the test field surface 124 which is inherently difficult to wet normally.

As described above, it has been found to be advantageous, surprisingly, for very small capillary gaps 132 to be used, i.e., capillary gaps 132 having a very small gap width h. Said gap width h should be 10 µm or less. This can, for example, as indicated in FIG. 3, be set by using distance elements 150 which determine the gap width h. In the case of very small gap widths, the distributor element 126 with its distributor surface 130 can also be directly applied to the test field surface 124, and so the capillary gap 132 is determined solely by surface roughnesses of the test field surface 124 and/or of the distributor surface 130. Thus, the capillary gap 132 according to the invention can also be produced by directly placing the distributor surface 130 on top of the test field surface 124, and this shall also be comprised by the term according to the invention of capillary gap 132. In contrast to current test strips based on capillary concepts, such as those for electrochemical test strips for example, an unopen system is formed in this way. This is indicated by the exemplary embodiment according to FIGS. 2A and 2B, but can, for example, also be realized in the exemplary embodiments according to FIGS. 1 and/or 3. The free test field surface 124, i.e., the region of the test field surface 124 which is accessible from the capillary gap 132 for the sample 114, can, for example, have an area of 5 mm×4 mm.

Figure 4:
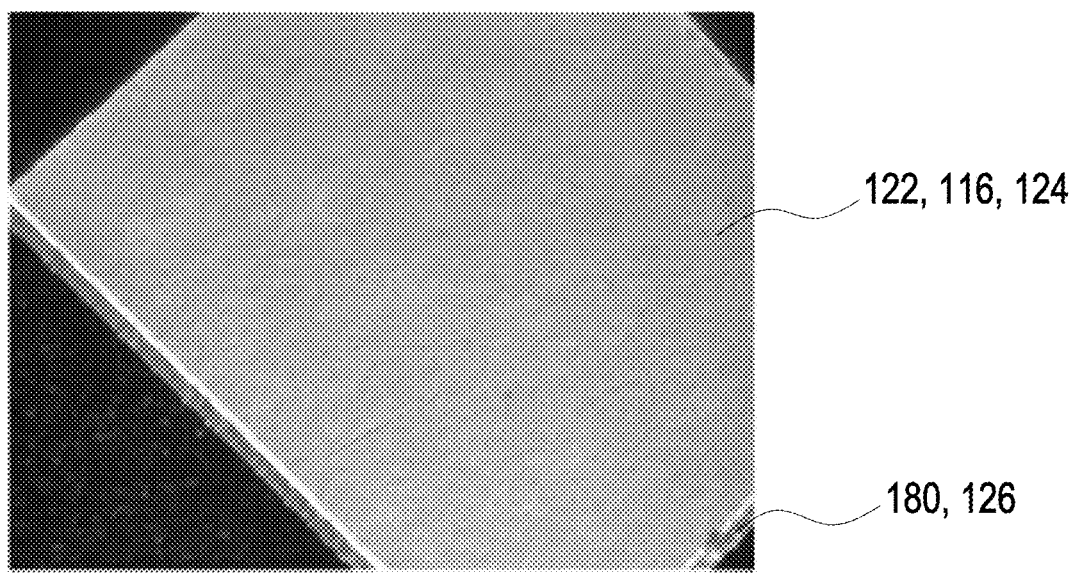
FIGS. 4A and 4B show an example of wetting a capillary gap with water.
Figure 4:
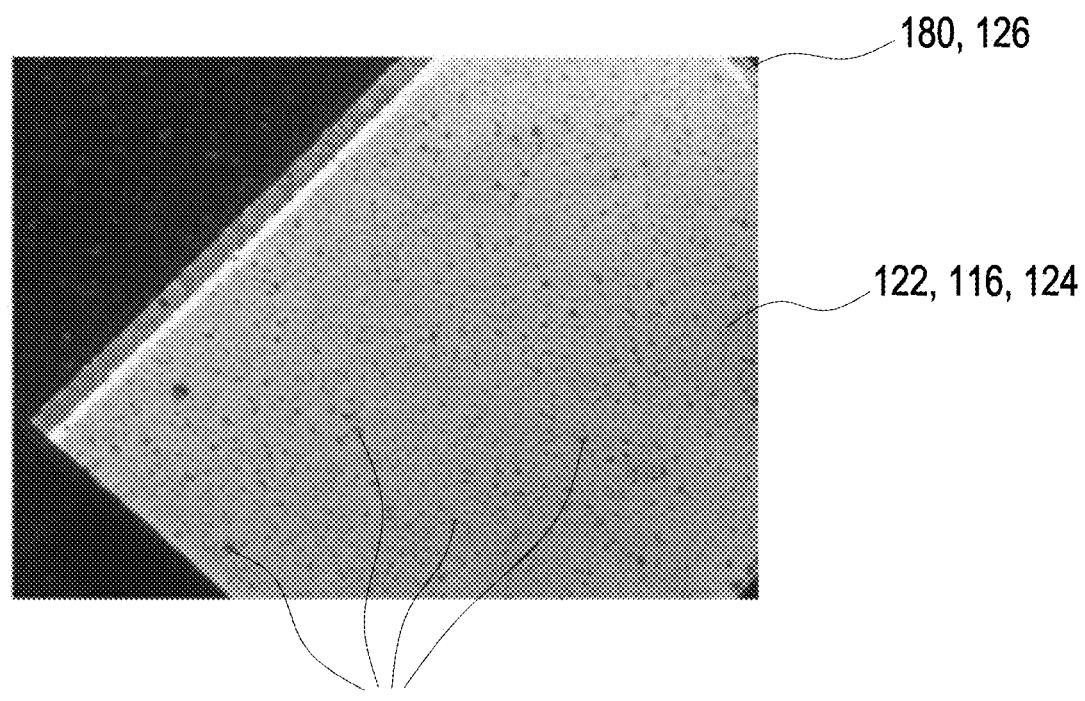

An example of an efficient wetting by using a capillary gap 132 is depicted in FIGS. 4A and 4B. A test field 116 having an area of 5 mm×4 mm was contacted with a slide 180 made of glass, such that said slide 180 completely covers the test field surface 124 of the test field 116. The slide 180, in this simple experiment, assumes the role of the distributor element 126. The images in FIGS. 4A and 4B show a layer structure which comprises the following layers listed going into the drawing plane: a POKALON® film as support element 122, a test field 116, and the slide 180. The pictures are illuminated from an angle of 45°. FIG. 4A shows the system of this kind before the introduction of water, whereas FIG. 4B shows the structure after the wetting with water. For this wetting, about 1 µl of water was applied as a drop at the edge of the structure. This drop spread across the arrangement in about 1 s. Thus, the wetting time is, as is explained further below, less important compared to other kinetics of the test element, i.e., is usually not the rate-limiting step, for example compared to the diffusion processes described in more detail below. The image in FIG. 4B was taken about 5 s after application of the water drop. Here, over the entire area, one can clearly recognize distributed pores 182 which verify the wetting with water. In contrast, a test strip having a POKALON® support element 122 and a test field 116 applied thereto, without a slide 180 applied thereto being used, wetted at times only poorly within the mentioned 5 s, if additional measures are not taken, such as the use of spreading meshes for example.

The experiment in FIGS. 4A and 4B therefore shows an exemplary embodiment of a test element 110 according to the invention in which the distributor surface 130 is placed directly on top of the test field surface 124, i.e., for example analogously to the exemplary embodiment according to FIGS. 2A and 2B. However, as described above, the other exemplary embodiments in FIGS. 1 and 3 can also be correspondingly modified. Such a test element 110, like in FIGS. 2A and 2B for example, therefore represents a "closed" system in which the capillary gap 132 is generated only by surface roughnesses. However, as described above, distance elements 150 can optionally and additionally be used. The measurement can, as described above, be carried out from different directions, for example parallel to the lateral extent of the test field surface 124 and/or perpendicular thereto, as has been described above for example. Combinations of the measurement methods are also possible. Owing to the preferably uniform distance between distributor surface 130 and test field surface 124, the fluid volume per unit area will hardly vary at the wetted sites, and a robust measurement is enabled with a correspondingly homogeneous test field 116. Since the system is optionally closed, this also contributes to the robustness. The preferably parallel surfaces 124, 130 further guarantee in many cases a complete absorption of the sample material, and so small sample volumes can also be made use of very effectively.

Overall, the proposed test elements 110 having gap widths h of 10 µm or less, especially in the form of closed systems having a distributor surface 130 applied directly to the test field surface 124, can lead to a considerable improvement in the spreading behavior. In addition, such test elements 110 can save space. Owing to the uniform rapid wetting of the sample 114 over the wetted area, rapid kinetics of the analyte-specific reaction can be achieved. This can be advantageous in particular for fluorescence measurements in which, in open systems, as is explained in more detail below, the detection substances, more particularly fluorophores, cannot be registered or only insufficiently because they diffuse away, and this can lead to changes in the signal behavior.

As explained above, the effect of the capillary gap 132 has a particularly positive impact when the test field material 118 of the test field 116 has a small grain size, preferably a grain size in the range of 50 nm to 5 µm. Such a small average grain size can, for example, be achieved by grinding.

This grain size in the preferred range results in different effects. A first effect is depicted in comparative experiments in FIGS. 5A and 5B. These comparative experiments show test fields 116 having a test field surface 124 onto which a drop of a sample 114 is applied. Panels 184 in FIGS. 5A and 5B each show microscopic images of the test field surface 124, whereas panels 186 show a change in gray values in the microscope images 184 along an intersection line 188 through the drop of the sample 114. The sample used was a test fluid having a concentration of 500 mg/dl glucose.

Figure 5A:
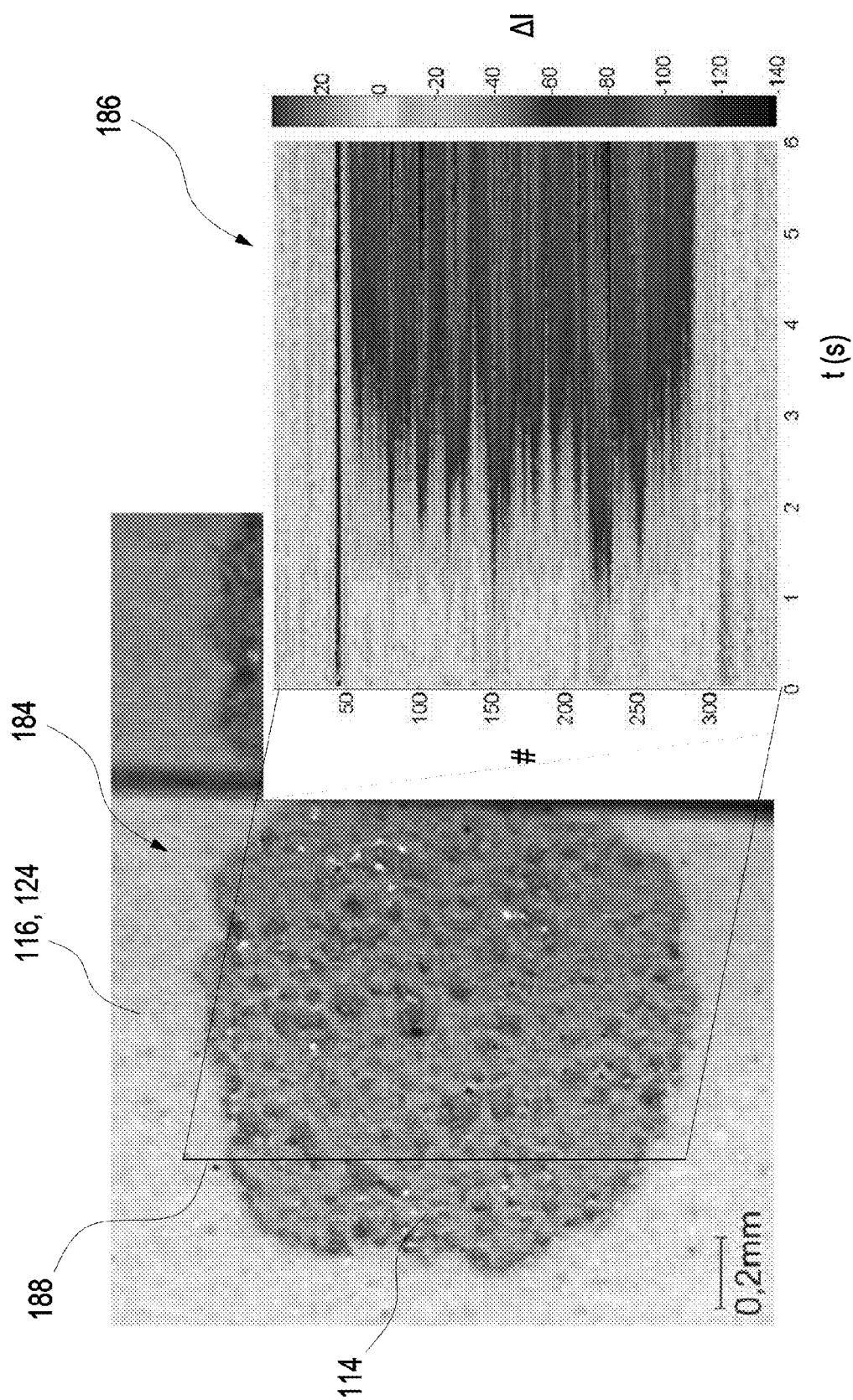
FIGS. 5A and 5B show examples of the wetting of a test field surface having an ungrinded test field material and a grinded test field material.
Figure 5:
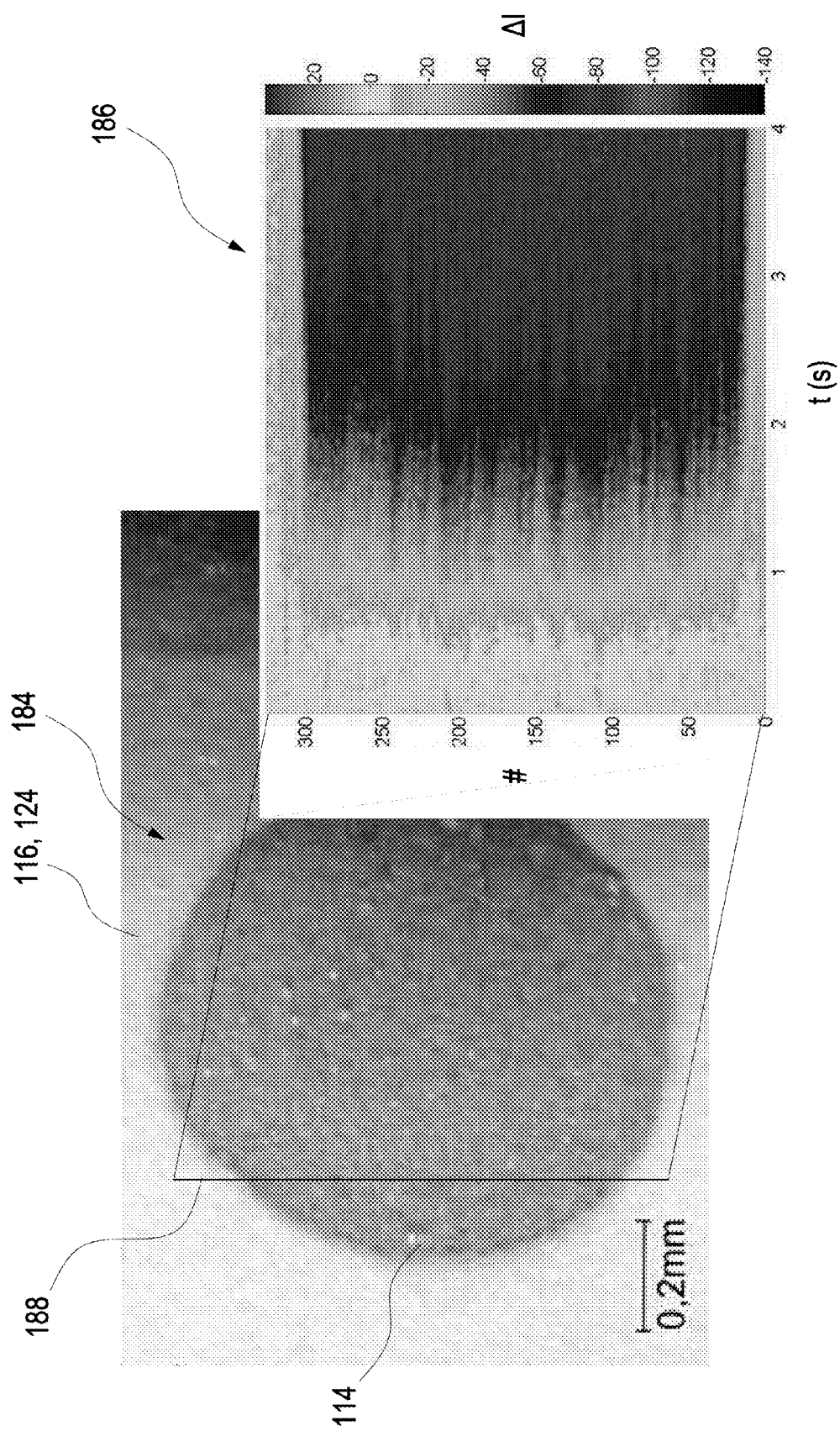

In panels 186, the pixel position, indicated by #, along the intersection line 188 is plotted on the vertical axis in arbitrary units. The horizontal axis specifies the time t in seconds after application of the sample 114. In panel 186, the changes in gray values are depicted in each case. On the right of this panel, there is a scale which specifies the change in gray value ΔI in arbitrary units. FIG. 5A shows a test field surface 124 having an ungrinded test field material 118, as is currently used in commercially available test strips. By contrast, FIG. 5B shows a test field 116 having a grinded test field material, the grain sizes of which are in the above-specified preferred range.

Without going into numerical details of the measurement, particularly panels 186 in FIGS. 5A and 5B show in a direct comparison that the grinding of the test field material 118 leads to a distinctly more homogeneous temporal change in the remission characteristics along the intersection line 188. Accordingly, the initiation of the reaction, which is specific for the detection of the analyte to be detected, is effected virtually at the same time along the intersection line 188 in the exemplary embodiment according to FIG. 5B, whereas in the experiment with ungrinded test field material 118 according to FIG. 5A, a strong temporal offset of the initiation of the reaction can be found locally. Thus, a temporal offset between individual locations along the intersection line 188 can occur which can be up to 3 s or more. Also, there can be observed locations along the intersection line 188 at which the reaction occurs instantaneously, and also locations at which the reaction does not appear to proceed at all.

Overall, it can therefore be established that an evening-out of the course of the analyte-specific reaction can be observed as the first positive effect of using a grinded test field material 118, and also overall a homogenization of said reaction across the wetted test field surface 124.

Furthermore, the experiments shown in FIGS. 5A and 5B were also carried out with test elements 110 which comprised a capillary gap 132 according to the invention. Some of these experiments are shown by way of example in FIGS. 6A and 6B. These figures each show the change in gray values ΔI in a remission measurement in arbitrary units as a function of the time t in seconds. The measured values were averaged over the area. FIG. 6A shows experiments with test elements 110 according to the invention having ungrinded test field materials 118, and FIG. 6B shows experiments with grinded test field materials 118 having grain sizes in the above-described preferred range of between 50 nm and 5 μm. Both experiments were carried out on test elements 110 having gap widths h of about 10 μm. Different glucose control solutions were used, having concentrations of 0 mg/dl (curves 190), 90 mg/dl (curves 192), 200 mg/dl (curves 194), 300 mg/dl (curves 196), and 500 mg/dl (curves 198).

Firstly, it can be seen in both FIGS. 6A and 6B that, from the time of application of the sample 114 (indicated by the reference number 200 in FIGS. 6A and 6B), which was arbitrarily defined as time "zero", there occurs a signal change which eventually approaches an end value characteristic of the concentration. As is apparent from a comparison of FIG. 6B, in which experiments with grinded test field material 118 are depicted, with the curves for ungrinded test field material 118 in FIG. 6A, the end value, surprisingly, is reached considerably more quickly with test elements 110 having grinded test field material 118 than in experiments with ungrinded test field material 118. Similar comparative experiments were also carried out with different gap widths h. In table 1, the results of these comparative experiments are again roughly summarized.

TABLE 1

End points of the change in gray values for different gap widths and grinded and ungrinded test field materials

| Concentrations [mg/dl] | 10 μm gap width, test field material ungrinded | 10 μm gap width, test field material grinded | 100 μm gap width, test field material grinded |
|---|---|---|---|
| 90 | 5.8 | 3 | 3.8 |
| 200 | 6.6 | 3.4 | 5.4 |
| 300 | 6.6 | 3 | 5.4 |
| 500 | 6.2 | 3.8 | 5.8 |

The first column of table 1 shows in each case the concentrations of the control solutions. The second column shows the end points in seconds, i.e., the times at which the end values were reached, for test elements 110 having gap widths of about 10 μm and ungrinded test field material 118, corresponding to the curves in FIG. 6A. The third column shows experiments with gap widths of about 10 μm in the case of grinded test field material 118, corresponding to the curves in FIG. 6B. The fourth column shows end points for test elements 110 having gap widths of about 100 μm, wherein grinded test field materials 118 were likewise used.

The results in table 1 clearly show that grinded test field materials 118 and gap widths of 10 μm or less are found to be optimal. For such test elements 110, the end points are close to 3 s, whereas for other experimental structures, considerably higher end points are found. Therefore, it can be established overall that the above-described preferred gap widths, more particularly in combination with grinded test field materials 118 having the described preferred grain sizes, can lead to the measurement being considerably sped up.

Figure 10:
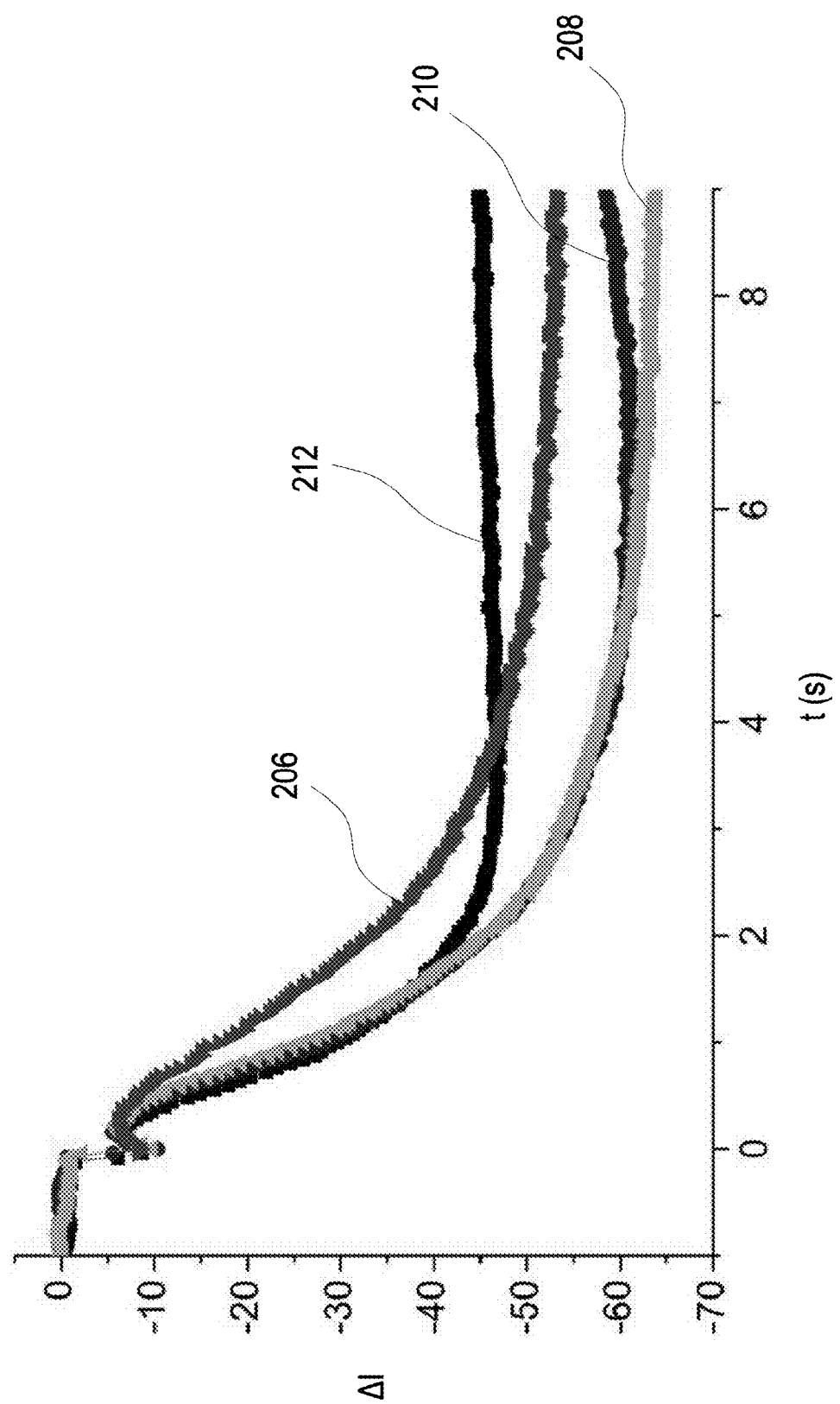
FIG. 10 shows changes in gray values as a function of time for test elements having different gap widths.

FIG. 10 depicts, analogously to the measurements in FIG. 6A and FIG. 6B, a series of experiments in which different gap widths were compared to one another. Again, the change in gray values ΔI in arbitrary units is plotted as a function of time t in s. In each case, aqueous glucose solutions having a concentration of 200 mg/dl were used. As a comparative experiment, a test element 110 without a capillary gap 132 was used at first, i.e., having a free, uncovered test field surface 124. This curve is indicated by the label 206 in FIG. 10. This measurement thus describes conventional test elements 110 in which a free drop is applied to a test field surface 124.

The further measurement curves indicate experiments with test elements 110 having capillary gaps 132. Curve 208 indicates a test element 110 having a gap width of 100 μm, curve 210 indicates a test element 110 having a gap width of 60 μm, and curve 212 indicates a test element 110 having a gap width of 10 μm. Throughout, test elements 110 having grinded test field materials 118 were used. Curve 212 thus corresponds to curve 194 according to FIG. 6B.

Apart from further specifics of the quantitative progression of curves 206 to 212, these comparative results again show the effect already described above, viz. that the end point of the measurements is attained considerably more quickly for small gap widths of 10 μm or less than for larger gap widths. Thus, the end point again is reached as early as after about 2 to 3 s for curve 212, whereas for the remaining curves 206 to 210, the end point is attained only much later, after 5 s or longer. This again shows clearly in a direct comparison the advantage of the small gap widths according to the invention with regard to the speed of the measurements.

Figure 7:
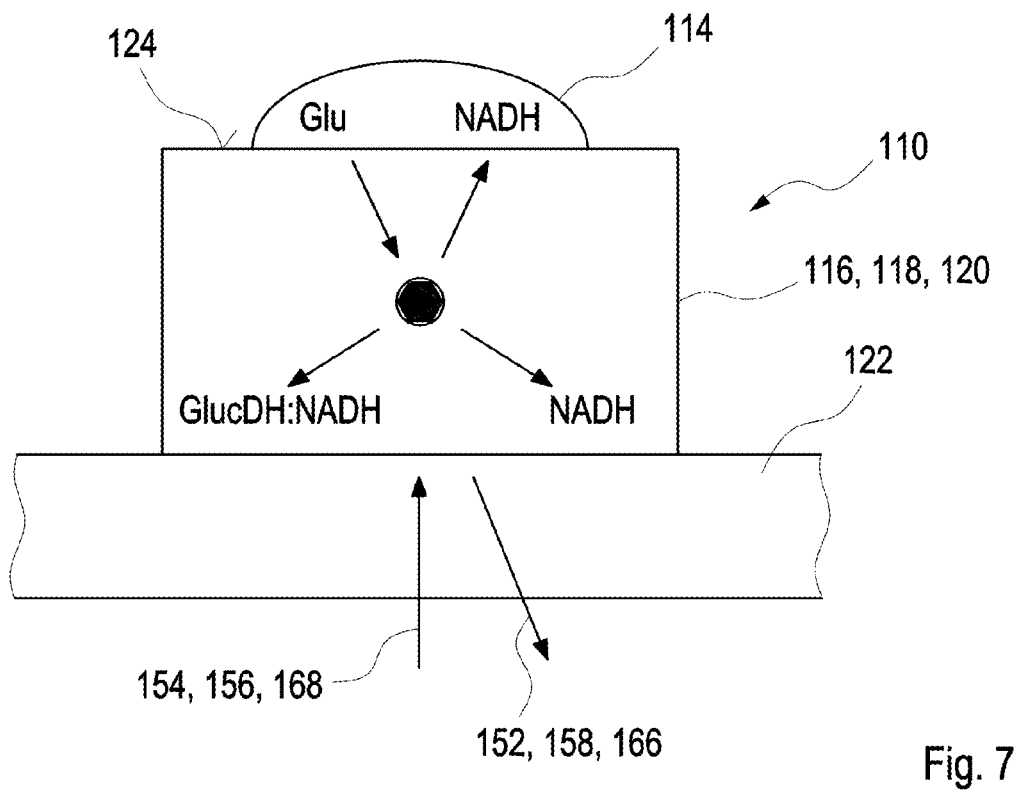
FIG. 7 shows an illustration of diffusion effects on a test field surface.

The detection reagent 120 can, for example, as described above, comprise glucose dehydrogenase (GlucDH), which reacts with penetrating glucose (indicated by Glu in FIG. 7) and induces a color change by means of a dye. Said color change can be recorded by means of a remission measurement, symbolized in FIG. 7 by the illuminating beam 156 and the remitted beam 158. However, as an alternative or in addition, the detection reagent 120 can also comprise glucose dehydrogenase and NAD+, which forms NADH as a fluorophore under the influence of glucose. Said fluorophore can be detected photometrically, and this is depicted in FIG. 7 by the beams 154, 156 and 152, 158. At the same time however, in the experiments, but not carried out in test equipment up to now, luminescence measurements were also carried out, and this is depicted in FIG. 7 by the beams 154, 168 and 152, 166. In both cases, NADH can act as a fluorophore.

However, NADH can, as depicted symbolically in FIG. 7, be present in different forms. One possibility is that NADH is present in a complexed form inside the test field 116, for example as a complex with glucose dehydrogenase (GlucDH), which is indicated by GlucDH:NADH in FIG. 7. To a lesser extent, NADH in the test field 116 can also be present in a free form. However, at the same time, NADH can also diffuse into the sample 114 and be present there in a free form, and this is likewise depicted symbolically in FIG. 7.

Particularly time-resolved fluorescence measurements are suitable for distinguishing between bound NADH (GlucDH:NADH) and free NADH. Such time-resolved fluorescence measurements can utilize the fact that the fluorescence of free NADH has a lifetime $\tau_1$ of about 0.4 ns, whereas complexed NADH (GlucDH:NADH) has a lifetime $\tau_2$ of about 3 ns. The luminescence thus has overall a decay behavior which is additively composed of both luminescences:

$$I_{Lumi} = A_1 \cdot \exp[-t/\tau_1] + A_2 \cdot \exp[-t/\tau_2].$$

Figure 8:
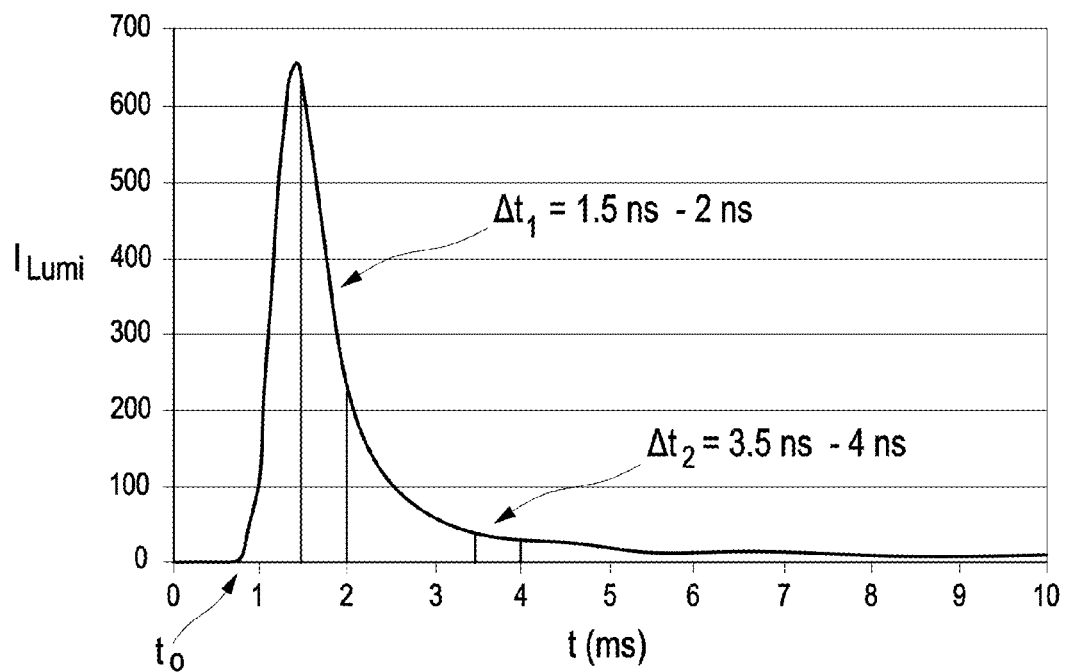
FIG. 8 shows temporal development of fluorescence from free and bound NADH.

$I_{Lumi}$ indicates the luminescence intensity, t indicates the time, $\tau_1$ and $\tau_2$ indicate the decay times of the respective luminescences, and $A_1$ and $A_2$ indicate starting intensities. The decay behavior of such a combined luminescence is depicted in FIG. 8. The luminescence intensity $I_{Lumi}$ in arbitrary units is plotted as a function of the time t in ns. At time $t_0$, an excitation event takes place.

In addition, FIG. 8 depicts a measurement in two time windows. A first time window $\Delta t_1$ is arbitrarily in an interval between 1.5 and 2 ns. Said time window was selected such that the excitation event has largely ended at the beginning of said time window, with the luminescence within said time window $\Delta t_1$ still being largely composed of both luminescences, since the end point of the interval is still not substantially greater than the smaller of the two lifetimes, in this case $\tau_1$.

A second time window $\Delta t_2$ was selected between 3.5 ns and 4 ns. Since the starting point of said time window of 3.5 ns is comparatively large compared to the fluorescence lifetime $\tau_1$ of free NADH of 0.4 ns, the luminescence in said second time window $\Delta t_2$ is practically composed only of the luminescence of the bound NADH (GlucDH:NADH), which has a lifetime of about 3 ns.

Figure 9:
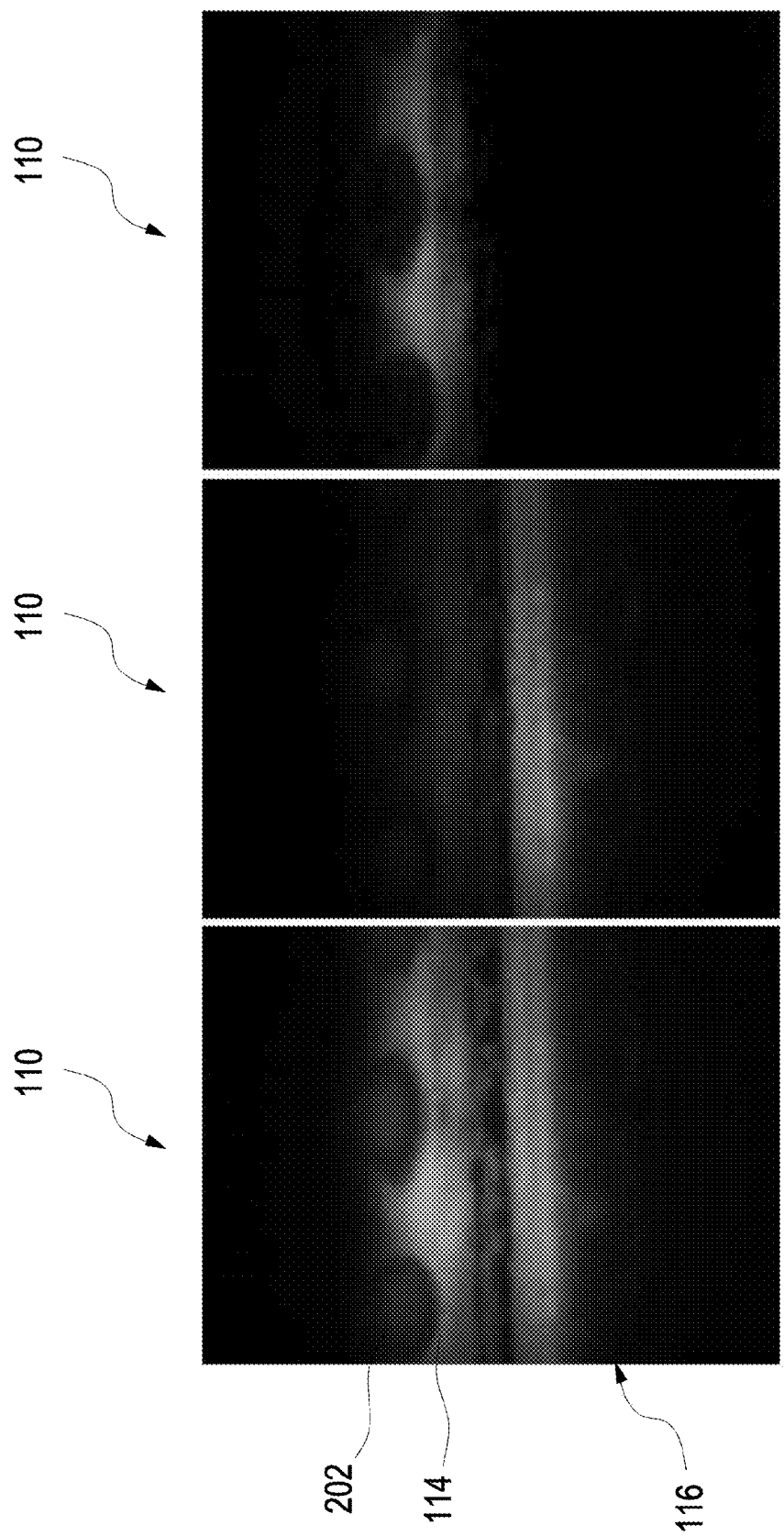
FIGS. 9A to 9C show cross-section images of a test element to illustrate a separation of the luminescence from free and bound NADH.

By means of such time-resolved measurements, it is therefore possible to separate the luminescence of free NADH from the luminescence of bound NADH. In order to demonstrate that this principle of separation works, time-resolved and spatially resolved luminescence measurements were carried out on conventional test elements 110, which measurements are depicted in FIGS. 9A to 9C. FIG. 9A shows a measurement in the time window $\Delta t_1$ between 1.5 and 2 ns, FIG. 9B shows a measurement in the time window $\Delta t_2$ between 3.5 and 4 ns, and FIG. 9C shows a difference image from FIGS. 9A and 9B.

For these experiments, which are merely intended to elucidate the measurement principle, use was made of commercial test elements 110. The test elements 110 comprise, over the test fields 116, spreading meshes 202 which can be clearly recognized particularly in the image according to FIG. 9A. Therefore, a fluid phase of the sample 114 formed between the test fields 116 and the spreading meshes 202.

As is apparent from the image according to FIG. 9A, in the time window $\Delta t_1$, luminescence takes place both in the solid phase of the test field 116 and in the fluid phase of the sample 114 lying thereover. In the time window $\Delta t_2$, depicted in FIG. 9B, it can be observed that there is, by contrast, only still luminescence from the region of the test field 116, but no longer from the region of the fluid sample 114. By means of the difference image depicted in FIG. 9C, it is therefore possible to subtract out from these measurements the luminescence of the free NADH having the shorter fluorescence lifetime $\tau_1$. FIG. 9C thus shows fluorescence which is caused almost exclusively by free NADH.

The theoretical considerations and said measurements, which are, however, independent of the invention and to the correctness and completeness of which the invention is not bound, show that diffusion effects of the free fluorophore NADH, or when using other types of detection substances of these detection substances, can be considerably important during detection. Since diffusion into the fluid phase of the sample 114 takes place to a considerable extent, the time courses of said diffusion can considerably impair the measurements. As a result of this, both the measurements in FIGS. 6A and 6B and in FIG. 10 and the results in table 1 can be at least qualitatively explained. At the beginning of the wetting with the sample 114, multiple processes take place, between which an equilibrium must be reached first, before a stable end point in the measurements, for example according to FIGS. 6A and 6B, is attained. One of these processes is the diffusion of the detection substance NADH into the fluid sample. Said diffusion occurs owing to a concentration difference between the test field 116 and the fluid sample 114. Only when a diffusion equilibrium has been reached, are there stable concentration ratios which lead to a stable end point in the measurements shown in FIGS. 6A and 6B. Owing to the smaller layer thickness of 10 μm compared to the 100 μm shown in table 1, the amount of the fluid column of the sample 114 available above the test field surface 124 is smaller for the small gap widths, and so a shorter period elapses until the fluorescence equilibrium is reached. Particularly for the back remission measurements indicated in FIG. 7, which are also plotted in FIGS. 6A and 6B, measurements are normally made of only NADH in a free or bound form within the test field 116, but not of free NADH within the fluid sample 114. A more rapid attainment of the diffusion equilibrium for smaller gap widths therefore also leads to the end point of the photometric remission measurements being attained more rapidly than for larger gap widths.

Optionally, this effect can be utilized in a device 112 according to the invention and in a process according to the invention in order to increase the reliability of the measurements. This can be achieved by considering the proportion of the detection substance in the sample 114 outside the test field 116 during the analysis of the measurements, for example the proportion of free NADH in the fluid blood sample 114. As described above, this can, for example, be achieved by a time-resolved measurement, for example a time-resolved measurement in different time windows which consider the different decay behaviors of the detection substances within the test field 116 and within the fluid sample 114. Since most detection reactions are well studied theoretically and empirically, the decay behaviors of the detection substances in different environments are also generally known.

However, when the detection substance in the sample 114 outside the test field 116 is determined at least qualitatively, but preferably quantitatively, for example in relation to the detection substance within the test field 116, then this allows the exactness of measurement of the detection of the analyte to be improved. For one thing, the measurement time can be adapted, since, as described above, the appearance of the end point depends on the gap width, which in turn, however, correlates with the absolute length of detection substance in the fluid sample 114 over the test field surface 124. In this way, for example, the measurement time, which should come after the end point, can be selected accordingly, for example automatically. However, as an alternative or in addition, a correction of the measured results can also take place, since the detection substance within the fluid sample 114 outside the test field 116, as described above, is normally no longer available for the detection of the analyte. Once this proportion has been determined, it is possible, for example, to perform a correction of the test results by means of appropriate correction factors.

In order to implement a measurement process which considers the detection substance in the sample 114 outside the test field 116, for example according to one or both of the above-described options, the device 112, for example according to FIG. 1, can comprise in particular a calibration device 204. Said calibration device 204, which is indicated merely symbolically in FIG. 1 and is connected there optionally and bidirectionally to the photometric measurement device 160 and to the luminescence measurement device 170, can, for example, also be completely or partially integrated into a central controller of the device 112. For example, the calibration device 204 can be completely or partially integrated in data processing equipment and can be completely or partially implemented by programming. The calibration device 204 can, for example, comprise one or more memory units in which correction factors or other correction algorithms are stored so that an analysis of the measurement can be carried out, taking account of the detection substance in the sample 114 outside the test field 116. In this way, the process according to the invention and the embodiment according to the invention of the device 112 make it possible to carry out, for example, calibrations to a gap width h, and so production-related variations of said gap width h can be compensated for by online calibrations. The calibration can, for example, be carried out before the actual measurement and/or during the actual measurement and/or after the actual measurement.

LIST OF REFERENCE NUMERALS

110 Test element for detecting an analyte in a sample
112 Device for detecting an analyte in a sample
114 Blood drop, sample
116 Test field
118 Test field material
120 Detection reagent
122 Support element
124 Test field surface
126 Distributor element
128 Film element
130 Distributor surface
132 Capillary gap
134 Detection part
136 Coupling part
138 Slot
140 Upper retaining piece
142 Lower retaining piece
144 Coupling body
146 Light guide
148 Light guide
150 Distance elements
152 Detection light
154 Interrogation light
156 Illuminating beam
158 Remitted beam
160 Photometric measurement device
162 Light source
164 Detector
166 Luminescence light
168 Excitation beam
170 Luminescence measurement device
172 Light source
174 Detector
176 Detection region
178 Application site
180 Slide
182 Pores
184 Microscope image
186 Change in gray values
188 Intersection line
190 0 mg/dl
192 90 mg/dl
194 200 mg/dl
196 300 mg/dl
198 500 mg/dl
200 Application, sample
202 Spreading meshes
204 Calibration device
206 Without capillary gap
208 Gap width 100 μm
210 Gap width 60 μm
212 Gap width 10 μm

What is claimed is:

1. A device for detecting at least one metabolite or other analyte in a body fluid or other sample, wherein the device comprises:
at least one test element for detecting the at least one metabolite or other analyte in a body fluid or other sample, the test element comprising at least one test field having a test field surface, wherein the test field comprises at least one detection reagent which is set up to carry out at least one detectable reaction that forms at least one detection substance in the presence of the metabolite or other analyte, wherein the test element is set up such that a stationary state of the detectable reaction is reached within a period of up to 4 seconds from an application of the body fluid or other sample; and
at least one calibration device, wherein the calibration device is set up to determine directly and/or indirectly the detection substance in the sample outside the test field and wherein the device is further set up to carry out the detection of the analyte taking account of said determination of the detection substance in the sample outside the test field.

2. The device of claim 1, wherein the device is set up to detect the detection substance in the sample outside the test field by means of at least one time-resolved measurement, more particularly by means of at least one time-resolved optical measurement.

3. The device of claim 1, wherein the test element comprises at least one capillary gap connected to the test field for receiving and distributing the sample on the test field, wherein the calibration device is set up to carry out a calibration of a gap width of the capillary gap by means of the detection of the detection substance in the sample outside the test field.

4. A process for detecting at least one metabolite or other analyte in a body fluid or other sample, using a device of claim 1, wherein at least one test element is used, wherein the test element comprises at least one test field having a test field surface for applying the sample, wherein the test field comprises at least one detection reagent which is set up to carry out a detectable reaction in the presence of the analyte, wherein the detection reagent is set up such that at least one detection substance is formed in the detectable reaction, wherein the detection substance in the sample outside the test field is determined directly and/or indirectly and wherein the detection of the analyte is carried out taking account of said determination of the detection substance in the sample outside the test field.

\* \* \* \* \*